United States Patent
Harding et al.

(10) Patent No.: US 6,908,459 B2
(45) Date of Patent: Jun. 21, 2005

(54) NEEDLELESS LUER ACCESS CONNECTOR

(75) Inventors: Weston F. Harding, Lehi, UT (US); Carolyn E. Brown, Salt Lake City, UT (US); Kelly D. Christensen, Centerville, UT (US); Tom M. Miner, Riverton, UT (US); Ralph L. Sonderegger, Farmington, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 271 days.

(21) Appl. No.: 10/017,024

(22) Filed: Dec. 7, 2001

(65) Prior Publication Data

US 2003/0109853 A1 Jun. 12, 2003

(51) Int. Cl.[7] ............................ A61M 25/16; A61M 5/00
(52) U.S. Cl. ........................................ 604/533; 604/256
(58) Field of Search ...................... 604/167.01, 167.02, 604/237, 256, 533, 905

(56) References Cited

U.S. PATENT DOCUMENTS

| | | | |
|---|---|---|---|
| 4,763,648 A | | 8/1988 | Wyatt |
| 4,809,679 A | * | 3/1989 | Shimonaka et al. ........ 600/154 |
| 4,920,970 A | | 5/1990 | Wyatt |
| 5,251,873 A | * | 10/1993 | Atkinson et al. ........ 251/149.1 |
| 5,279,583 A | | 1/1994 | Shober, Jr. et al. ......... 604/198 |

(Continued)

FOREIGN PATENT DOCUMENTS

EP 0 499401 4/1995

*Primary Examiner*—Brian L. Casler
*Assistant Examiner*—Lina Kontos
(74) *Attorney, Agent, or Firm*—Mony R. Ghose

(57) ABSTRACT

A needleless luer access connector is disclosed having a septum disposed in a housing. The septum has a proximal portion with a cross section, a medial portion with a cross section smaller than the cross section of the proximal portion, and a distal portion. A longitudinal slit extends through the septum from the proximal portion to the distal portion. The septum and housing are designed so that septum will not be rotated or removed from the housing when the connector is accessed by a male luer taper. In addition, the septum and housing are designed to bias the slit at the distal portion closed and so a male luer connector does not have to extend completely through the distal portion to open the slit at the distal portion. Finally, the septum and housing are designed to minimize the amount of dead space in the connector when accessed with a male luer taper.

7 Claims, 35 Drawing Sheets

U.S. PATENT DOCUMENTS

| | | |
|---|---|---|
| 5,389,086 A | 2/1995 | Attermeier et al. |
| 5,441,487 A | 8/1995 | Vedder .................. 604/167 |
| 5,531,711 A | 7/1996 | Attermeier et al. |
| 5,535,771 A | 7/1996 | Purdy et al. .................. 137/15 |
| 5,575,769 A | 11/1996 | Vaillancourt |
| 5,658,260 A | 8/1997 | Desecki et al. |
| 5,685,866 A | 11/1997 | Lopez .................. 604/249 |
| 5,694,686 A | 12/1997 | Lopez .................. 29/890.126 |
| 5,746,733 A | 5/1998 | Capaccio et al. .......... 604/411 |
| 5,755,696 A | 5/1998 | Caizza .................. 604/164 |
| 5,776,113 A | 7/1998 | Daugherty et al. ......... 604/280 |
| 5,785,692 A | 7/1998 | Attermeier et al. |
| 5,788,215 A | 8/1998 | Ryan .................. 251/149.6 |
| 5,797,897 A | 8/1998 | Jepson et al. |
| 5,832,971 A | 11/1998 | Yale et al. .................. 141/329 |
| 5,833,213 A | 11/1998 | Ryan .................. 251/149.1 |
| 5,873,862 A | 2/1999 | Lopez .................. 604/249 |
| 5,887,633 A | 3/1999 | Yale et al. .................. 141/329 |
| 5,901,942 A | 5/1999 | Lopez .................. 251/149.1 |
| 5,928,204 A | 7/1999 | Lopez .................. 604/249 |
| 5,950,986 A | 9/1999 | Daugherty et al. ...... 251/149.6 |
| 5,954,313 A | 9/1999 | Ryan .................. 251/149.1 |
| 5,957,898 A * | 9/1999 | Jepson et al. .................. 604/256 |
| 5,971,965 A | 10/1999 | Mayer |
| 6,050,978 A | 4/2000 | Orr et al. .................. 604/249 |
| 6,113,068 A | 9/2000 | Ryan .................. 251/149.4 |
| 6,132,403 A | 10/2000 | Lopez .................. 604/249 |
| 6,146,362 A | 11/2000 | Turnbull et al. |
| 6,158,458 A | 12/2000 | Ryan .................. 137/515.5 |
| 6,162,206 A | 12/2000 | Bindokas et al. |
| 6,171,287 B1 * | 1/2001 | Lynn et al. .................. 604/256 |
| 6,213,996 B1 | 4/2001 | Jepson et al. |
| 6,217,568 B1 | 4/2001 | Jepson et al. |
| 6,261,282 B1 | 7/2001 | Jepson et al. .................. 604/533 |
| 6,299,131 B1 | 10/2001 | Ryan .................. 251/149.1 |
| 6,344,033 B1 | 2/2002 | Jepson et al. |
| 6,364,847 B1 | 4/2002 | Shulze et al. |
| 6,447,498 B1 | 9/2002 | Jepson et al. |
| 6,569,125 B2 | 5/2003 | Jepson et al. |
| 6,572,591 B2 | 6/2003 | Mayer |
| 6,572,592 B1 | 6/2003 | Lopez |
| 6,605,076 B1 | 8/2003 | Jepson et al. |
| 6,635,044 B2 | 10/2003 | Lopez |

\* cited by examiner

FIG. 9
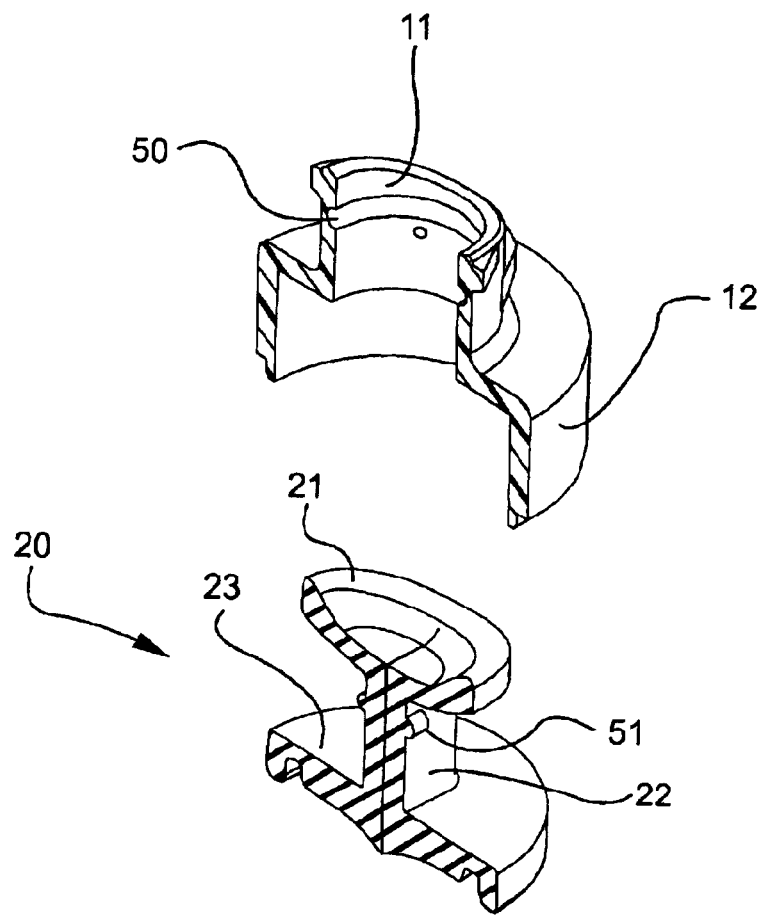
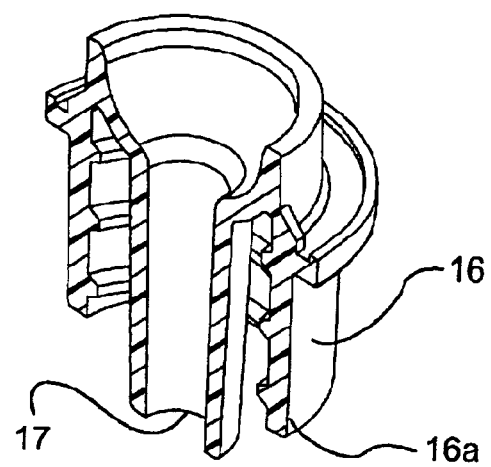

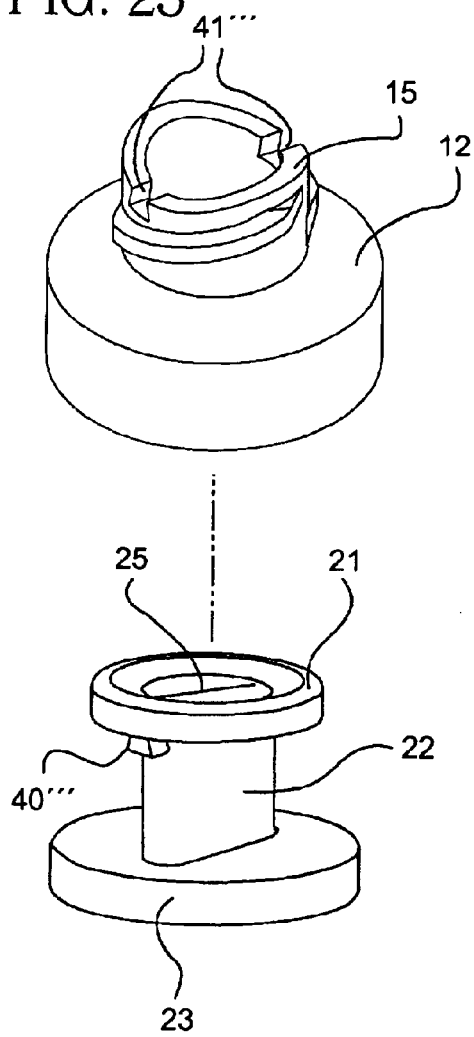
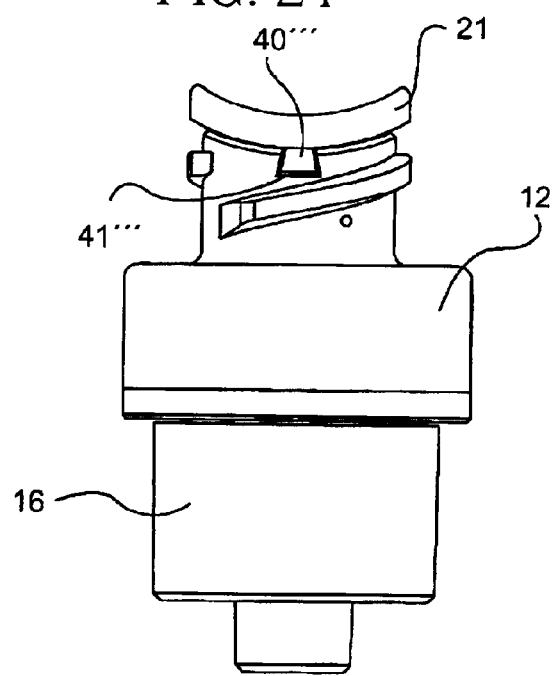

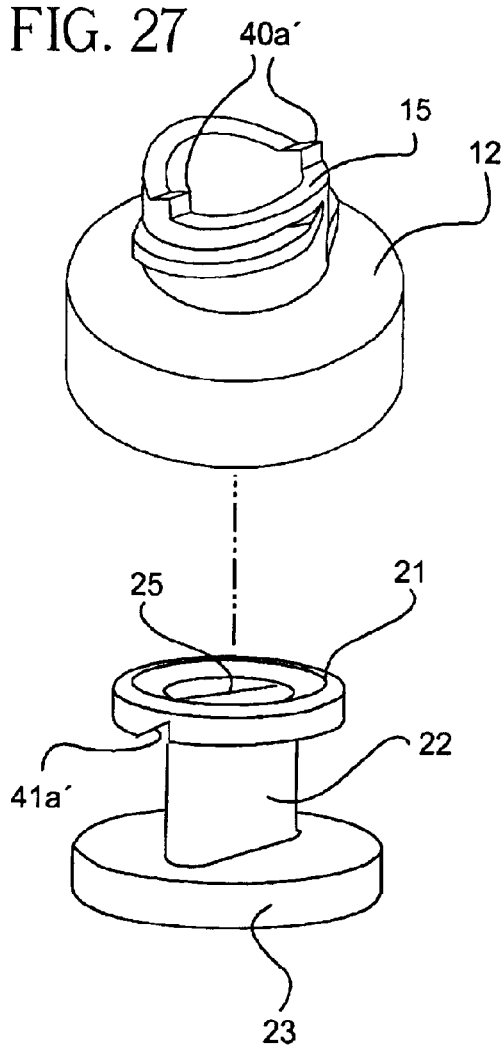
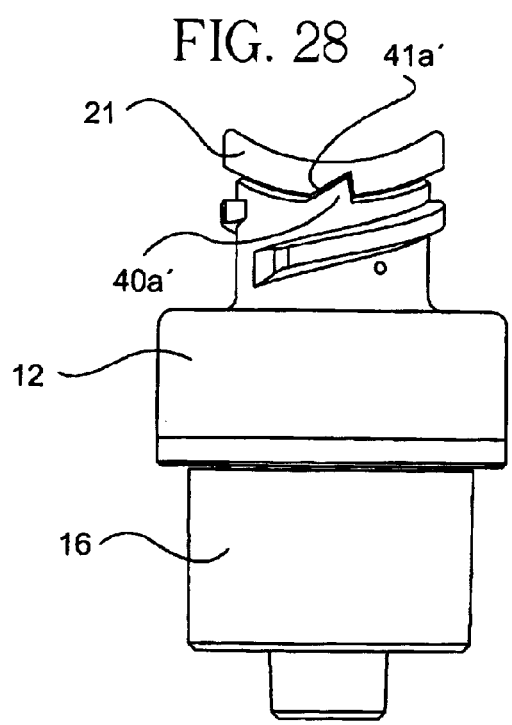

NEEDLELESS LUER ACCESS CONNECTOR

BACKGROUND OF THE INVENTION

The subject invention relates to a needleless connector referred to generally as a luer access device that allows a clinician to access a fluid flow line without the use of sharp needles. More particularly, the subject invention relates to a needleless luer access connector that may be opened by a standard male luer taper of a medical device, such as a syringe. The penetration of the connector by the male luer taper allows fluid flow through the connector. When the male luer taper is removed from the connector, it closes to prevent fluid flow therethrough.

In the treatment of patients, fluids are transferred between various containers and intravascular (IV) lines or through IV catheters into the patient through a closed system to prevent microbial ingress to the patient. During the course of such treatment where an IV catheter has been placed into a patient to gain access to the patient's vasculature, it may be necessary to infuse other fluids, such as medicaments, through the catheter into the patent or to withdraw blood from the patient for blood gas or other analysis. Such fluid withdrawal or injection into a patient may be through IV lines, saline wells, arterial lines, or hemodialysis lines. Previously, a rubber or silicone septum was used to cover an opening in the catheter or the IV line to prevent fluid from flowing out of the opening and to maintain a closed system. A clinician could access the opening by inserting a sharp needle from a syringe through the septum. This allowed the clinician to infuse fluid from the syringe into the patient or withdraw fluid from the patient into the syringe. The septum would reseal after the needle was withdrawn to prevent back flow of fluid.

In recent years, there has been great concern over the contamination of clinicians with a patient's blood or other fluid and a recognition that such "blood contaminated sharps" must be immediately disposed. This concern has arisen because of the advent of currently incurable and fatal diseases, such as Acquired Immune Deficiency Syndrome ("AIDS") and hepatitis, which can be transmitted by the exchange of body fluids from an infected person to another person. Thus, contact with the body fluid of an AIDS or hepatitis infected person must be avoided to prevent the transmission of such diseases to a healthy person. If a needle has been used to access an IV line in communication with an AIDS or hepatitis infected person, the needle is a vehicle for the transmission of the disease. Although clinicians are aware of the need to properly handle "blood contaminated sharps", unfortunately in certain medical environments, such as emergency situations or as a result of inattention or neglect, needlesticks with contaminated needles still occur. As a result of the problem of accidental needlesticks by "blood contaminated sharps", much effort has been expended in developing various connectors that avoid the use of sharp needles.

One type of needleless connector includes a longitudinally movable diaphragm that controls the flow of fluid through an internal cannula fixed in the connector. This internal cannula defines the fluid flow path through the connector. The movable diaphragm cooperates with a biasing member such as a spring or other flexible member that biases the top of the movable diaphragm toward the inlet or proximal opening to the connector. The opening is typically in the form of a female luer connection. When the movable diaphragm is adjacent to the inlet of the connector, the movable diaphragm occludes the opening to the internal cannula to close the connector to fluid flow. The connector can be opened when the clinician inserts the male luer taper of another medical device, such as a syringe, into the female luer portion of the connector. When this is done, the movable diaphragm is pushed down into the housing so the internal cannula extends through a pre-formed slit in the movable diaphragm providing a fluid flow path through the connector.

Although such connectors can generally operate in accordance with their intended function, such connectors could be improved. When the tip of the internal cannula engages the movable diaphragm, the internal cannula has a tendency to core the movable diaphragm. This may cause pieces of the movable diaphragm to be broken off and potentially infused into a patient. In addition, this coring of the movable diaphragm promotes fluid leakage of the connector and can result in a pathway for microbial ingress. Finally, the force needed to move the movable diaphragm past the tip of the internal cannula could be quite high making it difficult to operate and resulting in a substantial kickback force that tends to push the male luer taper back out of the connector.

A potential improvement to connectors with internal cannula are connectors that include a longitudinally movable diaphragm having a molded in opening through the diaphragm to control the flow of fluid through the connector. Some biasing member biases the movable diaphragm toward the inlet of the device. In this position, the proximal portion of the movable diaphragm is radially biased by the sidewalls of the housing defining the inlet opening of the connector to bias closed the molded in opening. This prevents fluid flow through the connector. When the clinician inserts the male luer taper of the syringe into the inlet of the connector, the movable diaphragm is moved down into the connector to an area that does not contact the proximal portion of the movable diaphragm. This allows the proximal portion of the diaphragm to return to its unbiased condition with the molded in opening in the open position to provide a fluid flow through the connector. Thus, these connectors do not need an internal cannula to extend through the diaphragm to provide the fluid flow path through the connector.

However, connectors having a molded in opening are not without problems. For example, the molded in opening in the movable diaphragm may not be tightly closed when in the inlet. This could result in leakage through the connector and provide a path for microbial ingress. In addition, the high activation force and kick back problems are not resolved because of the biasing mechanism that is still used in these types of connectors.

Yet another approach has been the development of a connector that can be accessed by a blunt cannula that is connected to the standard male luer taper of a standard syringe. Such a connector has a septum having a longitudinal slit extending through it disposed over an opening on a proximal end of the connector. The distal end of the connector includes a standard male luer taper so the connector can be connected to other medical devices and IV lines having a female luer connection. This type of connector cannot be accessed with a standard male luer taper because a standard male luer taper is too large to fit into the space in the opening not already occupied by the septum. Instead this type of connector is accessed by a blunt cannula that is narrower than a standard male luer taper and which can be attached to a standard male luer taper. When the clinician desires to access the medical device or IV line, a blunt cannula is placed on the syringe and is then inserted through the slit in the septum. This places the syringe in fluid communication with the medical device or IV line. After fluid is injected into or withdrawn from the patient, the syringe with the blunt cannula is removed from the septum. Because of the design of the connector, the slit in the septum closes and prevents the backflow of fluid through the device.

Although slit septum connectors that can be accessed by a blunt cannula work generally in accordance with their intended purpose they could be improved. For example, this type of connector requires that a separate blunt cannula be connected to the male luer taper of another medical device to allow the connector to be accessed. This requires excess inventory problems and adds costs to the health care facility using the connector. Moreover, the blunt cannula typically does not fill up the space in the housing of the connector when it is accessed. This leaves an annular "dead space" cavity in the housing between the sides of the blunt cannula and the inner walls of the housing. Residual blood may be left in this cavity and provide a breeding ground for various germs and microbes and is difficult to flush.

SUMMARY OF THE INVENTION

It is therefore an object of this invention to provide a connector that can be accessed without the use of a needle.

It is another object of this invention to provide a needleless luer access connector that is not prone to leakage or microbial ingress.

It is yet another object of this invention to provide a needleless luer access connector that minimizes the dead space volume therein.

It is still another object of this invention to provide a needleless luer access connector that does not require a high degree of force to access and minimizes the kickback force when the connector is accessed.

It is a further object of this invention to provide a needleless luer access connector that does not require any additional or special devices to access.

The needleless luer access connector of this invention includes a housing having a top portion and bottom portion with an inlet at the top of the top portion of the connector and an outlet at the bottom of the bottom portion of the connector. The inlet and top portion are designed and configured so that the needleless luer access connector of this invention can be connected to a standard male luer taper configuration of another medical device. Similarly, the outlet and bottom portion has a standard male luer configuration that can be connected to a standard female luer configuration of another medical device. A septum is located in the top portion of the connector to control fluid flow through the connector. The septum has an enlarged proximal portion, a narrowed elongated medial portion and an enlarged distal portion. The configuration of the narrowed elongated medial portion allows the needleless luer access connector of this invention to be accessed with a standard male luer taper. It is also designed to minimize both access and kickback force. A longitudinal slit is formed in the septum and extends through the proximal, medial and distal portions thereof. The transverse axis of the slit is preferably parallel to the major axis of the medial portion. The proximal portion of the septum projects above the top of the inlet and rests on the top surface of the sidewalls of the housing located at the periphery of the inlet. Preferably the top surface has two diametrically opposed high portions and two diametrically opposed low points to give the proximal portion of the septum a saddle like configuration. This saddle like configuration biases the slit closed along the proximal portion of the septum. This is one mechanism to ensure a tight seal to prevent leakage and microbial ingress. The distal portion of the septum is captured between the proximal portion and the distal portion of the housing.

When a male luer taper is pushed against the proximal surface of the septum, it deflects distally and laterally and allows the male luer taper to access the slit in the septum. In addition, the distal and lateral deflection of the septum forces the slit to open and allows the male luer taper to penetrate the septum through the slit. When the male luer taper is fully inserted into the septum, the slit is forced open along the entire length of the septum so that the septum allows fluid to flow through the connector. The needleless luer access connector of this invention is configured so that the male luer taper does not have to extend completely through the septum to completely open the slit at the distal portion of the septum. This is achieved by ensuring that the circumference of the distal portion of the septum is held in place by the housing and by increasing the mass along the distal portion of the septum. The increased mass at the distal portion of the septum is achieved by providing the distal portion of the septum with a radial dimension that is larger than the radial dimension of the medial portion of the slit. As a result of holding the circumference of the distal portion of the septum in place and the increased mass of the distal portion of the septum, the septum acts as a swinging door to fully open the slit when the male luer taper is inserted fully into the septum. The male luer taper can thereafter be removed from the septum allowing the septum to return to its prestressed state and close the connector to fluid flow.

The external surface of the medial portion of the septum may be formed with ribs that engage complementary ribs formed on the internal surface of the sidewalls of the housing. When the male luer taper is fully inserted into the septum the external surface of the medial portion of the septum engages the internal surface of the sidewalls of the housing. The ribs are located on the septum and the housing in the appropriate location so that when the septum is accessed by the male luer taper, the ribs on the septum engage the ribs on the housing. The interengagement of the ribs causes the septum to remain temporarily locked in place with respect to the housing. Once the male luer taper has been removed sufficiently from the septum so that the external surface of the medial portion of the septum no longer engages the internal surface of the sidewalls of the housing the ribs disengage to allow the septum to return to its prestressed state. This feature prevents the septum from being pulled out of the housing when the male luer taper is removed from the connector. Various configurations for the ribs could be used to achieve this effect. For example, complementary ribs and detents or grooves or slots could be formed on the exernal surface of the medial portion of the housing and the internal surface of the sidewalls of the housing. Alternatively, these features could be formed along the proximal portion of the connector instead of along the medial portion of the connector.

A variation of the foregoing feature is the use of various key and key hole configurations formed on the septum and the housing to prevent rotation of the septum during male luer access and removal. For example, the proximal portion of the septum could be formed with a key that fits into a keyhole formed along the proximal portion of the housing. The keys and key holes could have various complementary shapes. The only limitation is that the keys and key holes hold the septum against rotational movement with respect to the housing.

Another mechanism to facilitate the closing of the connector against fluid flow is to have the septum and housing configured so that the septum is compressed along the sides of the slit at least at the distal portion of the septum. Alternatively or concurrently, the septum and housing can be configured so that the septum is pulled in tension at the ends of the slit. This configuration provides a tight seal to prevent leakage and microbial ingress. In order to achieve this force distribution, the distal portion of the septum could be formed with a substantially circular cross section while the housing adjacent to the distal portion of the septum when the septum is in its prestressed condition could be formed with a substantially elliptical or oval cross section. If the slit is located so that it is aligned with the major axis of the ellipse, i.e. the transverse axis of the slit and the major axis of the ellipse are collinear or parallel, the slit will be biased to a closed position. The minor axis of the ellipse will tend to compress the sides of the slit together while the major axis of the ellipse will tend to place the ends of the slit in tension thus forcing the slit closed. This effect can also be achieved by forming complementary tabs and slots in the septum and housing that pull and push the septum in the appropriate directions. In addition, this effect can be achieved by forming the distal portion of the septum with a substantially elliptical or oval cross section and the relevant portion of the housing could be formed with a substantially circular cross section. With this configuration, the transverse axis of the slit should be collinear or parallel to the minor axis of the slit. This circle will tend to pull the minor axis apart and push the major axis together to close the slit.

The housing minimizes the amount of dead space by carefully matching the configuration of the distal portion of the septum when a male luer taper fully accesses the connector with the location and configuration of the sidewalls in the housing that form the fluid flow path through the connector. In other words, when a male luer taper is inserted into the needleless luer access connector of this invention, the distal portion of the septum is forced distally into the housing and occupies at least a portion of the space in the distal portion of the housing. The sidewalls in the connector are configured so they engage the distal portion of the septum that is displaced distally by the male luer taper. In this way, the sidewalls in conjunction with the distal portion of the septum minimizes dead space in the housing.

BRIEF DESCRIPTION OF THE DRAWINGS

The preferred embodiments are illustrated in the drawings in which like reference numerals refer to like elements and in which:

FIG. 9 is an exploded perspective view in cross section of the needleless luer access connector of this invention with a second embodiment of the septum and the housing;

FIG. 23 is an exploded perspective view of a portion of the needleless luer access connector of this invention showing a seventh embodiment of the septum and an eighth embodiment of the housing;

FIG. 24 is a side elevational view of the needleless luer access connector of this invention showing the seventh embodiment of the septum and the eighth embodiment of the housing;

FIG. 27 is an exploded perspective view of a portion of the needleless luer access connector of this invention showing a ninth embodiment of the septum and a tenth embodiment of the housing;

FIG. 28 is a side elevational view of the needleless luer access connector of this invention showing the ninth embodiment of the septum and the tenth embodiment of the housing;

DETAILED DESCRIPTION OF THE INVENTION

Figure 1:
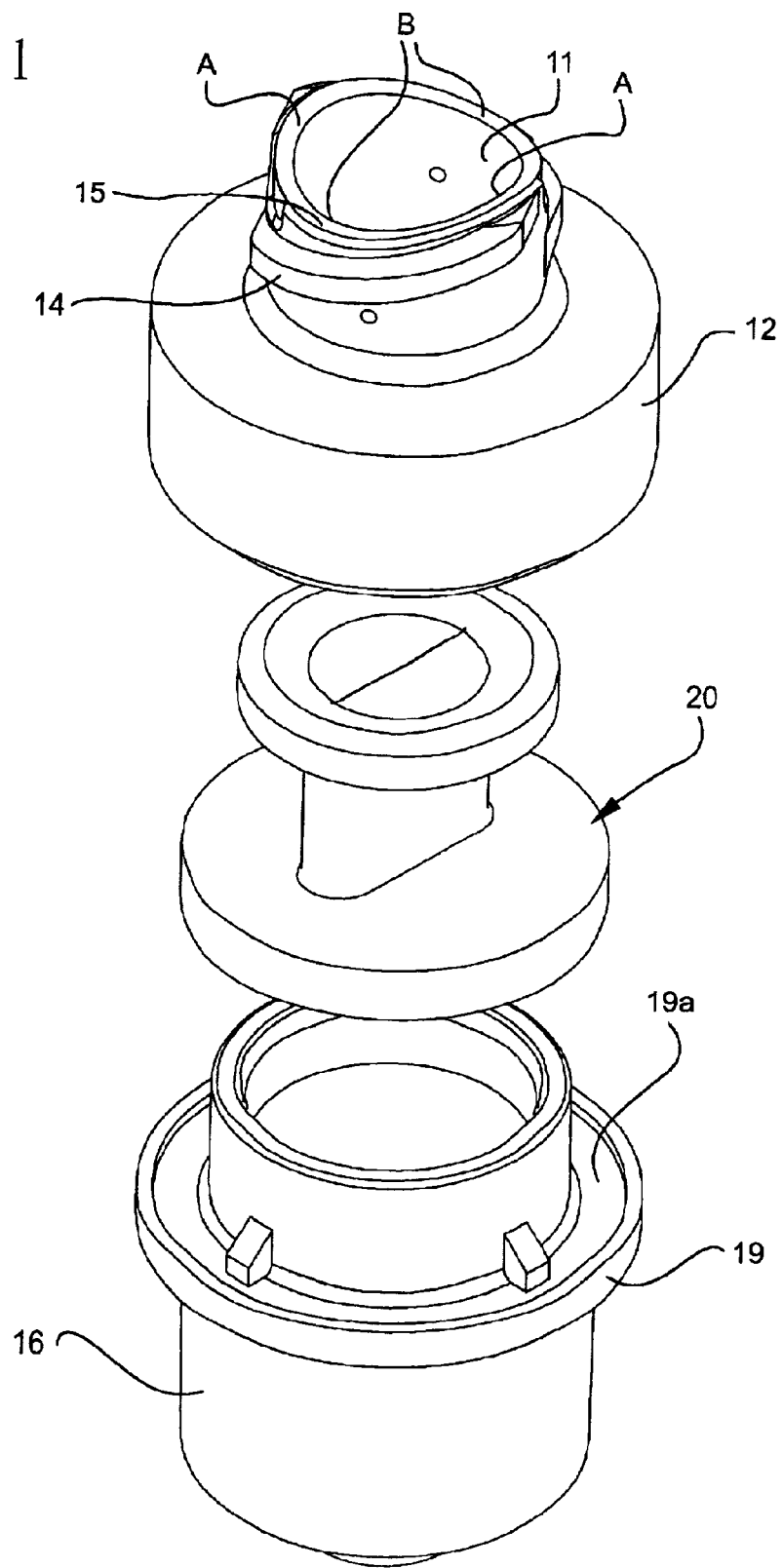
FIG. 1 is an exploded perspective view of the needleless luer access connector of this invention.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

The needleless luer access connector of this invention includes a housing 10 having a top portion 12 and bottom portion 16. Typically plastic materials such as polycarbonate, or PETG could be used to form housing 10. Housing 10 defines an inlet 11 and an outlet 17 with a cavity or bore 13 extending therebetween. Inlet 11 is defined at the top of top portion 12 and outlet 17 is defined at the bottom of bottom portion 16 of the needleless luer access connector. Inlet 11, and thus that portion of bore 13 adjacent to inlet 11 and that portion of top portion 12 adjacent to inlet 11, must be sized and configured in conformity with at least some of the International Standards Organization (ISO) standards for a female luer connection. This will allow a male luer slip or lock to be connected to inlet 11. Thus, inlet 11 has a maximum external diameter of about 0.265 inches (6.73 millimeters) and an internal diameter of about 0.214 inches (5.44 millimeters) to allow a male luer taper to extend into inlet 11. The exterior of the top of top portion 12 includes luer threads 14 that allow another medical device having a male luer lock to be connected to the top of proximal portion 12. Alternatively, no luer threads 14 need be formed on the exterior of the top of top portion 12 so that another medical device having a male luer slip can be connected to the top of top portion 12. Outlet 17, and thus that portion of bore 13 adjacent to outlet 17 is sized and configured as a male luer taper that complies with the ISO standards for a male luer taper. ISO standard 594-2:1998(E) requires that the male luer taper have a minimum length of about 2.953 inches (7.5 millimeters). Forming this part of housing 10 in accordance with ISO standards allows the needleless luer access connector of this invention to be connected to a standard female luer configuration of another medical device. If desired, a luer lock collar 16a may formed about the male luer taper to lock the connector to a female luer. In such a case, the luer lock should comply with ISO standards. According to ISO standards, the root diameter R of the thread on the male luer lock fitting should be about 0.315 inches (8 millimeters) and the crest diameter C of the thread on the male luer lock fitting should be about 0.276 inches (7 millimeters). In addition, the male luer taper must extend a minimum of about 0.083 inches (2.1 millimeters) past the end of luer lock collar 16a.

Figure 1A:
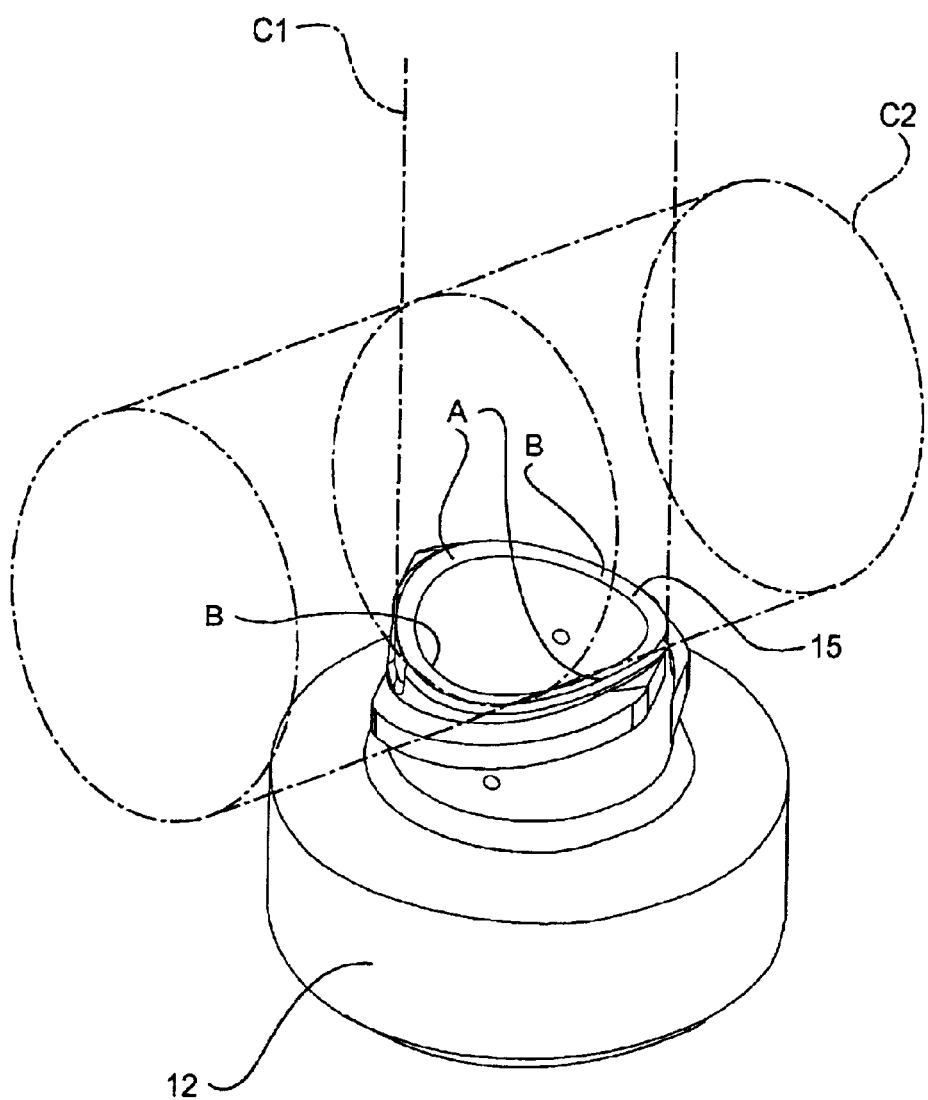
FIG. 1A is a perspective view of the top portion of the housing for the needleless luer access connector of this invention showing lines in phantom to help explain the shape of the top surface of the top portion.

As seen especially in FIG. 1, the top surface 15 of top portion 12 adjacent to inlet 11 transitions between two high points A and two low points B. Each high point A is about 180 degrees apart from each other and each low point B is also about 180 degrees apart from each other such that each high point A is about 90 degrees from each low point B. Preferably, each high point A should be greater than zero but less than about 0.050 inches (1.143 millimeters) higher than each low point B. Most preferably, each high point A should be about 0.027 inches (0.686 millimeters) higher than each low point B. To achieve a smooth circumferential top surface 15 that transitions in a smooth undulating fashion between high points A and low points B, top surface 15 can be formed by using a curved surface with a radius of about 0.30 inches (7.62 millimeters) as the template to cut the top of proximal portion 12. In geometric terms, the imaginary cylinder C1 defined by the top of proximal portion 12 can be cut with an imaginary cylinder C2 having a radius of about 0.30 inches (7.62 millimeters) oriented 90 degrees to the longitudinal axis of the imaginary cylinder C1 defined by the top of proximal portion 12. This results in top surface 15 having the shape described. By changing the radius of the imaginary cylinder C1, the distance between high points A and low points B can be changed. See FIG. 1A.

Figure 7:
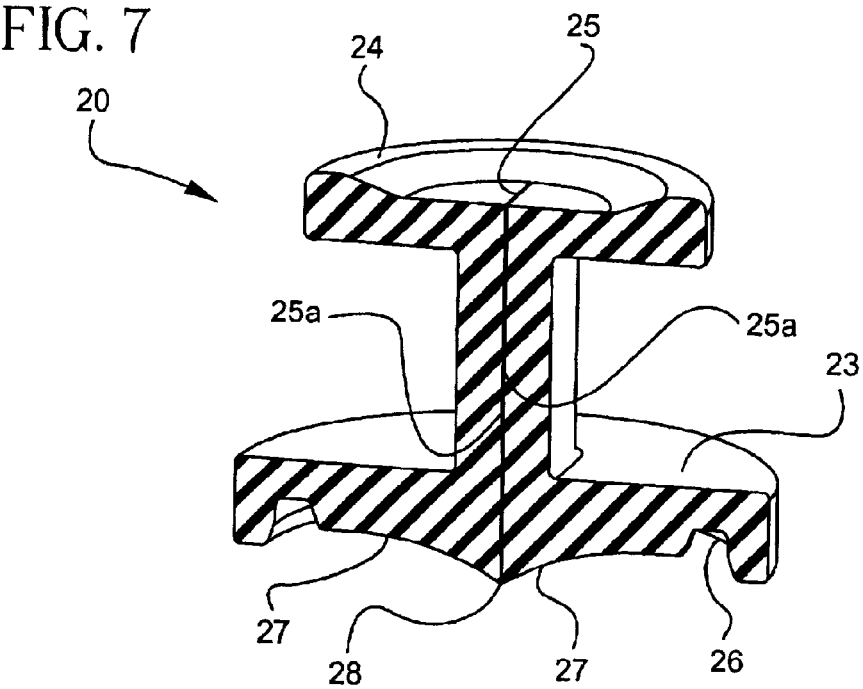
FIG. 7 is a perspective view in cross section of the first embodiment of the septum used in the needleless luer access connector of this invention.
Figure 8:
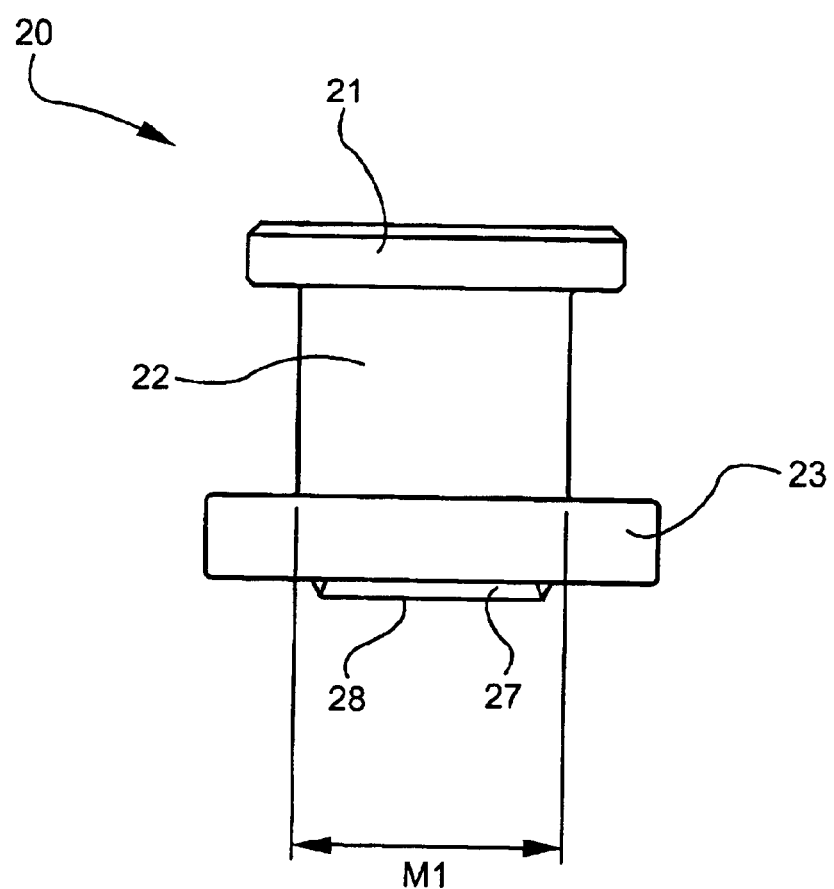
FIG. 8 is a side elevational view of the first embodiment of the septum used in the needleless luer access connector of this invention showing the major length of the medial portion of the septum.

A septum 20 is located in top portion 12 of the needleless luer access connector to control fluid flow therethrough. Typically materials such as silicone or polyisoprene could be used to form septum 20. Septum 20 has an enlarged proximal portion 21, a medial portion 22 and an enlarged distal portion 23. The top of enlarged proximal portion 21 can be formed with an annular lip 24 extending about the circumference of proximal portion 21. Lip 24 provides extra mass to give enlarged proximal portion 21 extra rigidity to prevent it from folding in when it is accessed by a male luer taper. Medial portion 22 has a cross sectional area that is smaller than the cross sectional area of proximal portion 21 and smaller than the cross sectional area of distal portion 23. Preferably medial portion 22 has a generally oblong cross-section with a major axis M1 substantially equal to the internal diameter of inlet 11. Alternatively, the major axis may be slightly greater than the internal diameter of inlet 11 to help ensure that septum 20 remains in inlet 11. The minor axis M2 of medial portion 22 is smaller than the diameter of proximal portion 21 and smaller than the internal diameter of inlet 11. Thus, medial portion 22 has a cross-sectional area that is smaller than the cross-sectional area of inlet 11. This provides a space between the external surfaces of medial portion 22 along the major axis thereof and the sidewalls of housing 10 that define inlet 11 where the material of septum 20 can be displaced when a male luer taper is disposed in septum 20. As seen in FIG. 7, enlarged distal portion 23 defines an annular slot 26 extending about the bottom thereof. In addition, an enlarged diametrical portion 27 extends across the bottom of enlarged distal portion 23.

Figure 5:
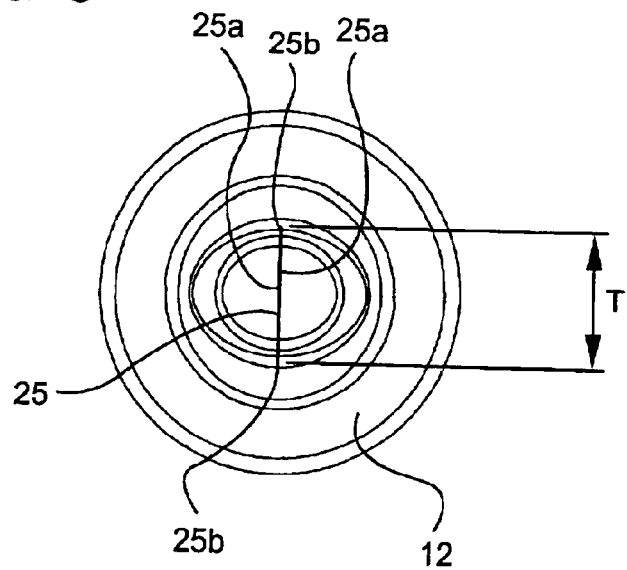
FIG. 5 is a top plan view of the needleless luer access connector of this invention shown in FIG. 4.
Figure 6:
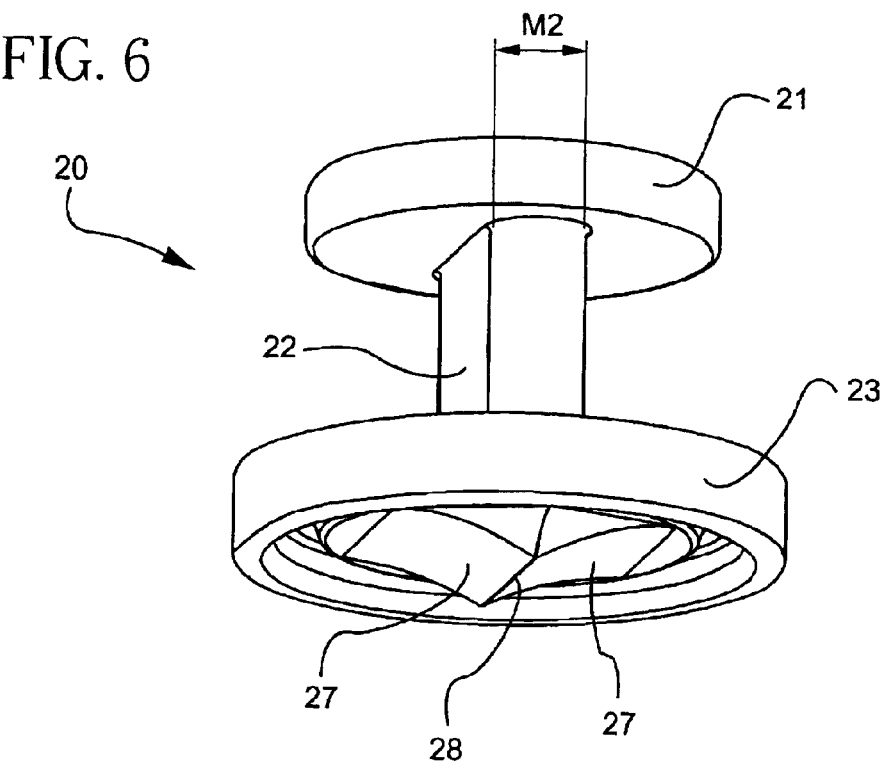
FIG. 6 is a perspective view of a first embodiment of the septum used in the needleless luer access connector of this invention.

A slit 25 is formed in septum 20 and extends longitudinally through proximal portion 21, medial portion 22 and distal portion 23. As seen in the top plan view of septum 20 of FIG. 5, slit 25 has a transverse axis T and is defined by a pair of sides 25a and a pair of ends 25b. Preferably, diametrical portion 27 of enlarged distal portion 23 extends from sides 25a of slit 25 along an apex 28 back to the bottom surface of enlarged distal portion 23. Diametrical portion 27 provides increased mass adjacent to the bottom of slit 25 to help keep slit 25 closed against fluid flow.

Septum 20 is disposed in top portion 12 of housing 10 such that enlarged proximal portion 21 rests on top of top surface 15. As a result, enlarged proximal portion 21 projects above the top of inlet 11. In addition, because of the undulating configuration of top surface 15, proximal portion 21 is pushed up along high points A. Septum 20 is aligned in housing 10 such that the middle of sides 25a of slit 25 are aligned with each of the high points A and transverse axis T is aligned with low points B. Thus the minor axis of medial portion 22 is aligned with high points A and the major axis of medial portion 22 is aligned with low points B. Distal portion 23 is captured between top portion 12 and bottom portion 16 of housing 10 such that preferably the top wall of bottom portion 16 engages annular slot 26 of septum 20. The bottom wall of top portion 12 is bonded to a circumferential flange 19 formed along a medial portion of bottom portion 23 adjacent to luer lock collar 16a. If desired, an annular slot 19a can be formed in flange 19 and the bottom wall of top portion 12 can be inserted into annular slot 19a. Any standard bonding technique, such as chemical adhesive or ultrasonic welding can be used to bond top portion 12 to bottom portion 16. Preferably, medial portion 22 is held in tension when septum 20 is located in housing 10. This tension in combination with portions of proximal portion 21 being lifted up by high points A on top surface 15 results in a compressive force being exerted against sides 25a to force slit 25 closed at least at the top of proximal portion 21.

Figure 2:
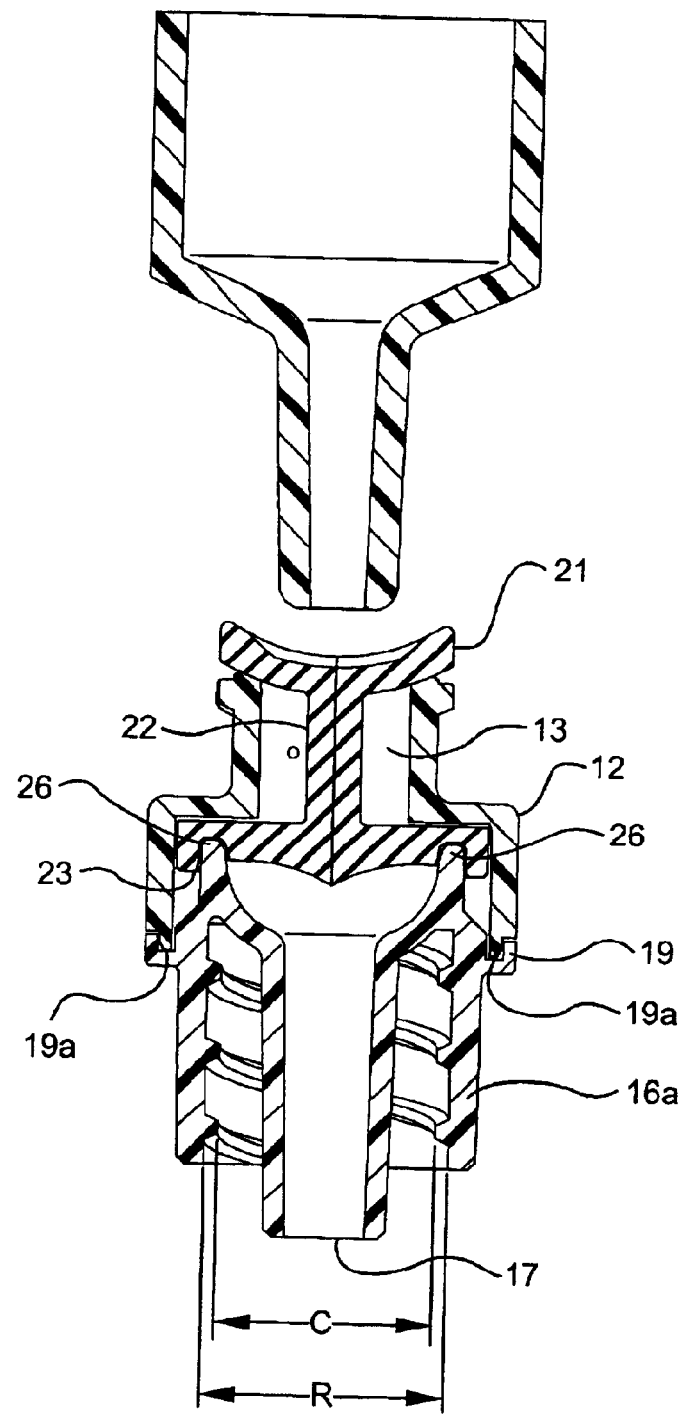
FIG. 2 is a cross sectional view of the needleless luer access connector of this invention closed to fluid flow and with a male luer taper of another medical device such as a syringe poised for penetration of the connector.
Figure 3:
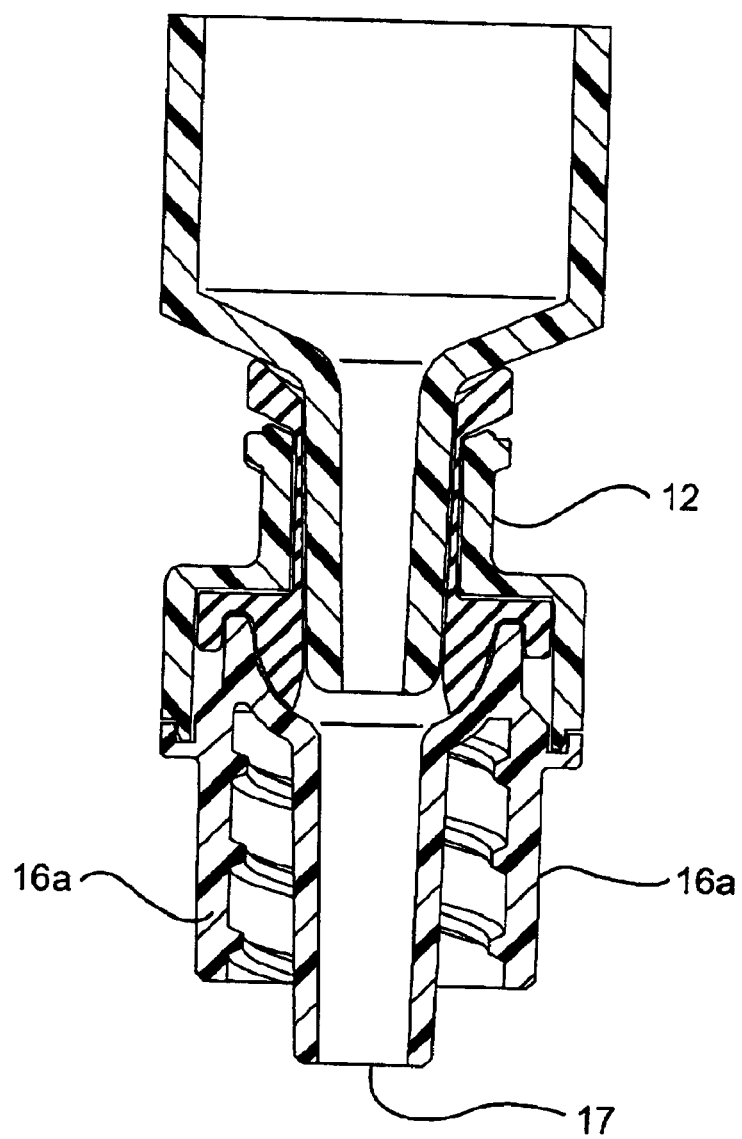
FIG. 3 is a cross sectional view of the needleless luer access connector of this invention with a male luer taper of another medical device such as a syringe disposed in the connector so that it is open to fluid flow.
Figure 4:
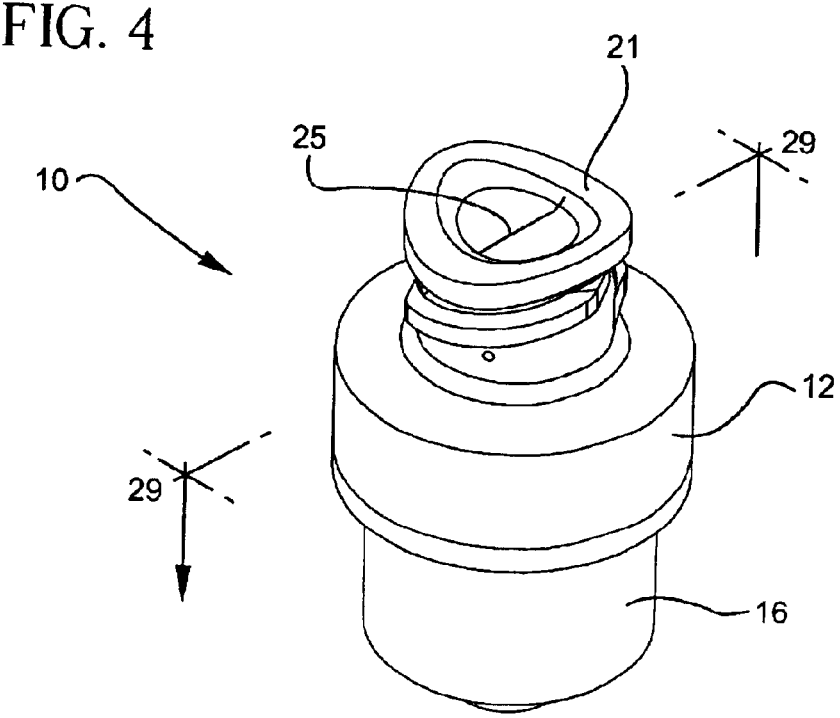
FIG. 4 is a perspective view of the needleless luer access connector of this invention.

When a male luer taper of another medical device, such as a syringe, is pushed against the top of proximal portion 21 of septum 20, proximal portion 21 deflects distally and laterally and allows the male luer taper to access slit 25 in septum 20. As the male luer taper is pushed further into slit 25, medial portion 22 also deflects distally and laterally. Compare FIGS. 2 and 3. By having a cross-section for medial portion 22 that is smaller than the cross-section of bore 13, space is provided inside bore 13 to allow such lateral deflection of medial portion 22. This distal and lateral deflection of septum 20 forces slit 25 to open and allows the male luer taper to penetrate septum 20 into slit 25. When the male luer taper is fully inserted into septum 20, slit 25 is forced open along the entire length of septum 20 and thus allows fluid to flow through septum 20 and the needleless luer access connector of this invention. Thereafter, the male luer taper of the other medical device can be withdrawn from slit 25. The inherent resiliency of septum 20 causes septum 20 to return to its normal unstressed state with slit 25 closed. This prevents any further fluid flow through septum 20.

Figure 10:
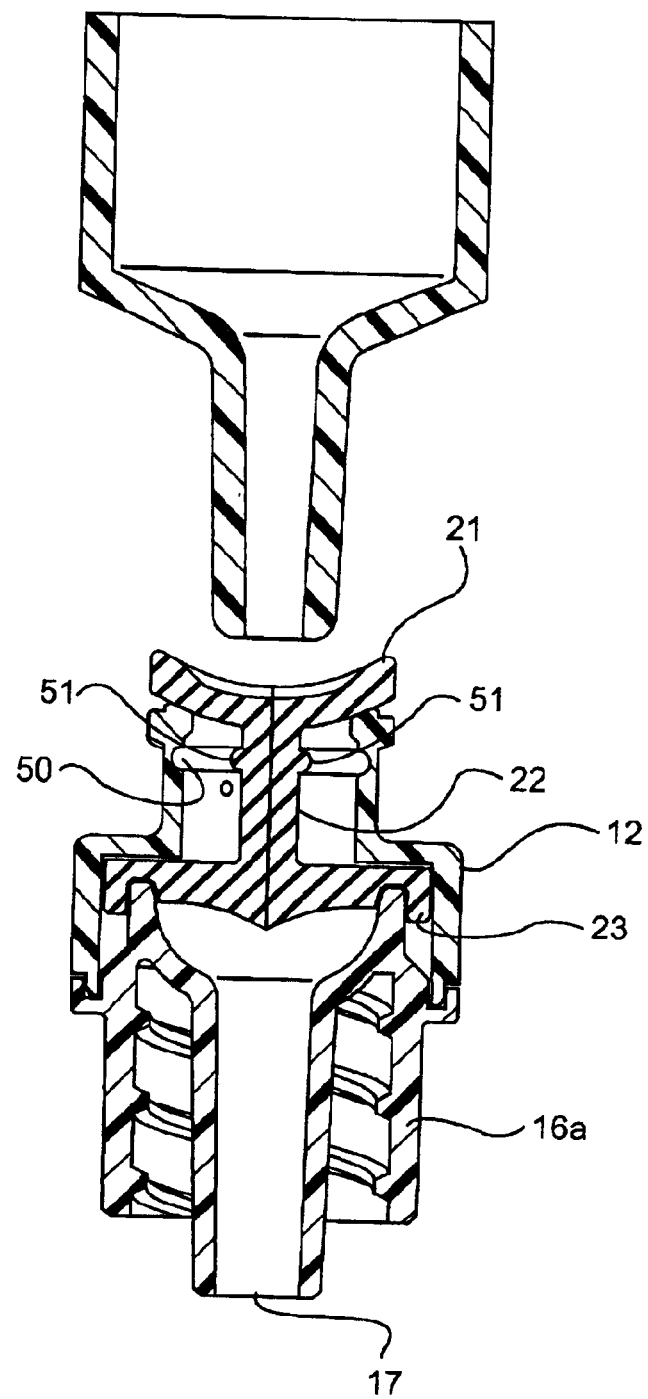
FIG. 10 is a cross sectional view of the needleless luer access connector of this invention with the second embodiment of the septum and the housing with a male luer taper of another medical device such as a syringe poised for penetration of the connector.
Figure 11:
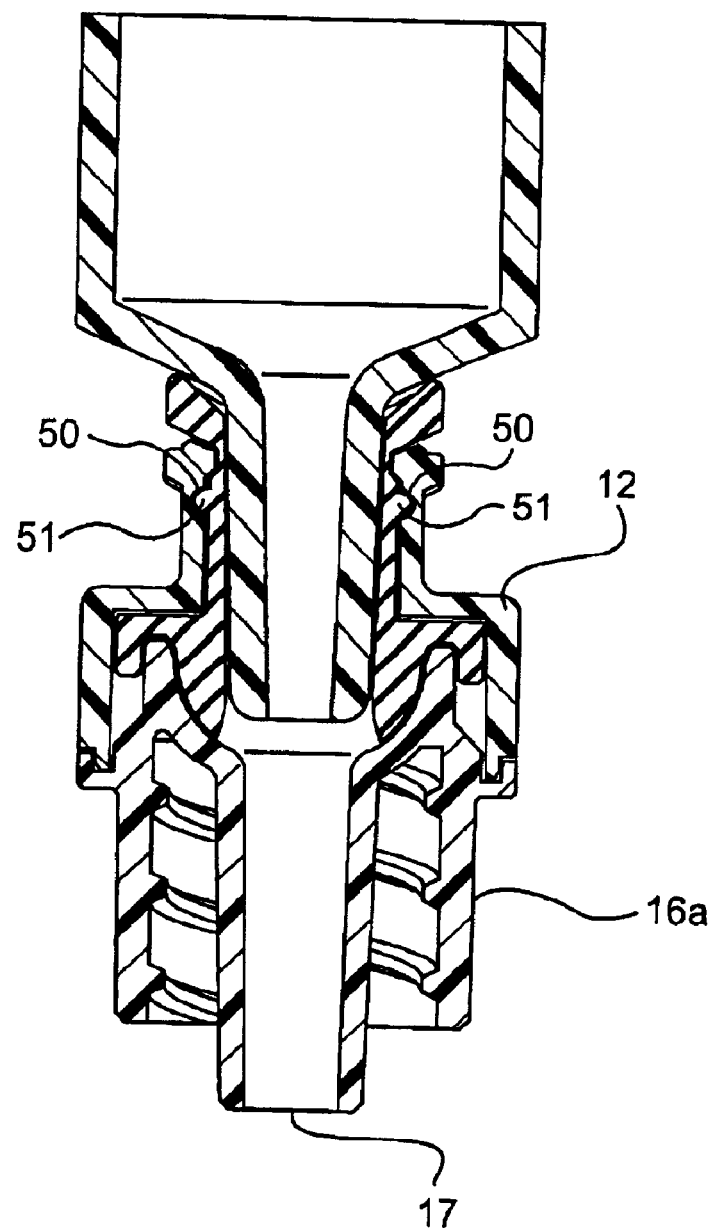
FIG. 11 is a cross sectional view of the needleless luer access connector of this invention with the second embodiment of the septum and the housing and a male luer taper disposed therein.

Because septum 20 may be formed from materials such as silicone or polyisoprene, it is possible for septum 20 to stick to the male luer taper and be withdrawn from housing 10 as the male luer taper is withdrawn from housing 10. In order to avoid this potential problem, top portion 12 of housing 10 and septum 20 may be formed with complementary catch features that hold proximal portion 21 of septum 20 in place. For example, a groove 50 extending at least partially about the circumference of the internal surface of top portion 12 could be formed adjacent to top surface 15. In such an embodiment, two grooves 50 could be located about 180 degrees apart on the internal surface of top portion 12 aligned with high points A. Alternatively, groove 50 could extend about the entire circumference of the internal surface of top portion 12. See FIGS. 9 through 11. A rib 51 could be formed along a portion of medial portion 22 and adapted to fit in groove 50. Preferably two ribs 51 are used and are located on either side of medial potion 22 about 180 degrees apart along the major axis of medial portion 22. Groove 50 would be located on either side of top portion 12 to engage ribs 51. Thus, when a male luer taper enters slit 25, medial portion 22 is displaced such that ribs 51 fit into grooves 50 to hold septum 20 in housing 10 until the male luer taper has been removed from septum 20. This interengagement between grooves 50 and ribs 51 avoids the potential problem of septum 20 sticking to the male luer taper and being withdrawn from housing 10 as the male luer taper is withdrawn from housing 10. Since grooves 50 and ribs 51 engage with one another when septum 20 is displaced laterally and distally by the male luer taper, the male luer taper can be removed from septum 20 without pulling septum 20 out of housing 10. The longitudinal location of grooves 50 and ribs 51 can be determined by simple routine experimentation to see where a portion of septum 20 engages the internal sidewall of proximal portion 12. The inherent resiliency of septum 20 allows grooves 50 and ribs 51 to disengage from each other once the male luer taper has been removed from septum 20 and thus allows septum 10 to return to its unbiased, i.e. unstressed state.

Figure 12:
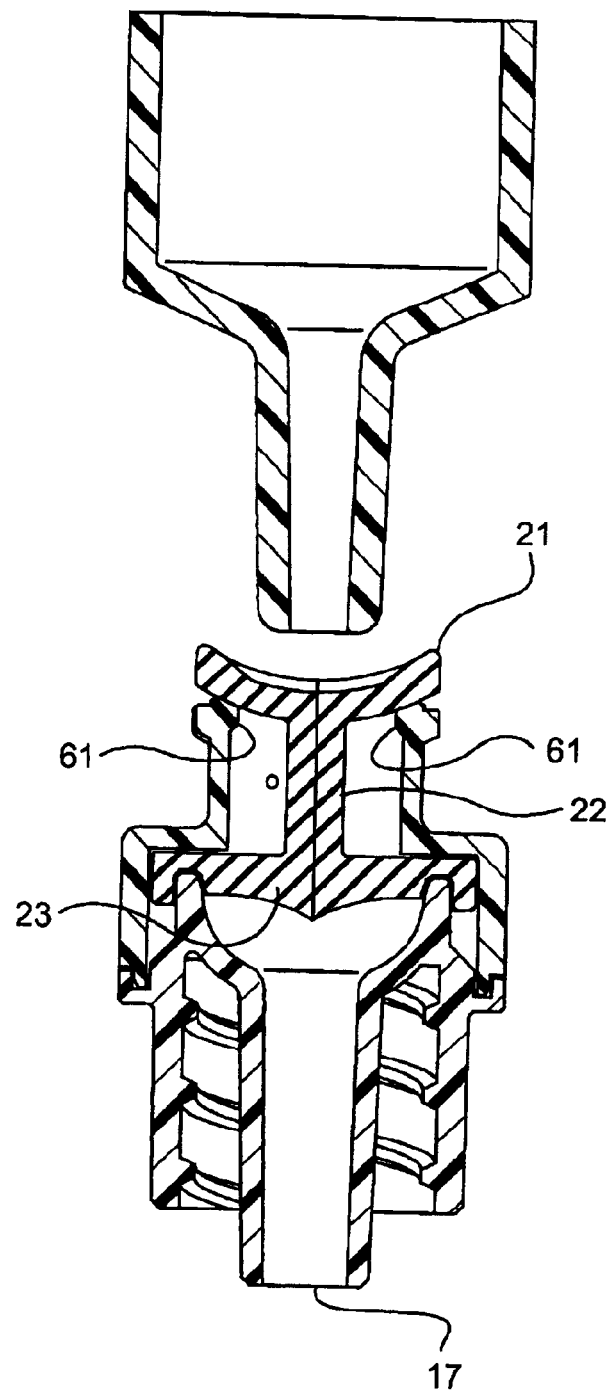
FIG. 12 is a cross sectional view of the needleless luer access connector of this invention with a third embodiment of the housing and a male luer taper of another medical device such as a syringe poised for penetration of the connector.
Figure 13:
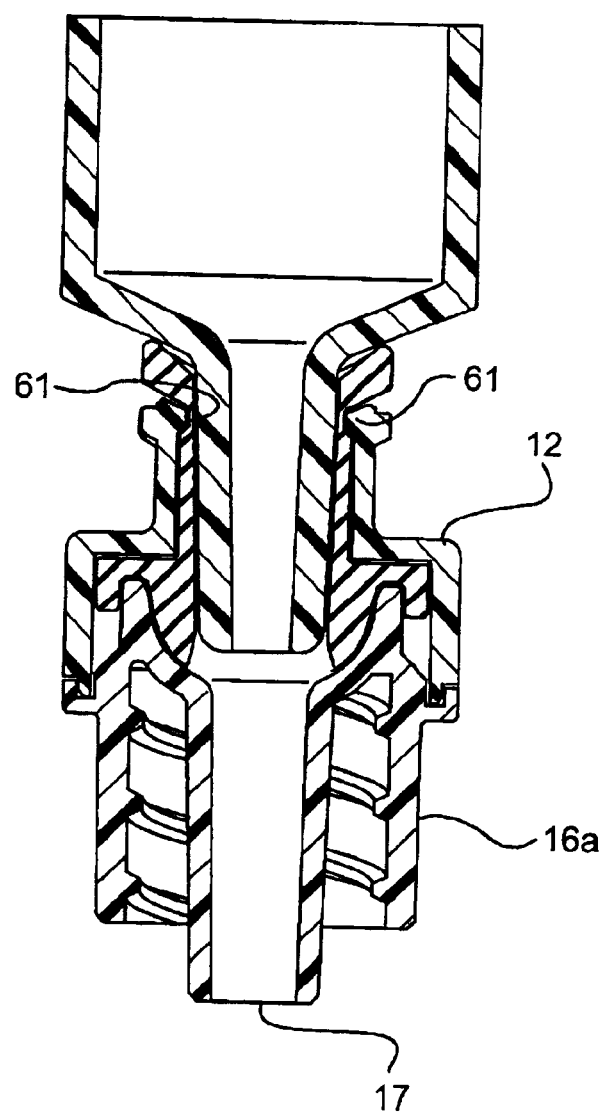
FIG. 13 is a cross sectional view of the needleless luer access connector of this invention with the third embodiment of the housing and a male luer taper of another medical device such as a syringe disposed in the connector so that it is open to fluid flow.

A variation of this configuration is shown in FIGS. 12 and 13 where at least one rib 61 is formed in top portion 12 adjacent to inlet 11 and extending into inlet 11. Preferably two ribs 61 are used and are located about 180 degrees apart so they are adjacent to high points A. Alternatively, one rib could be used that would extend about the entire circumference of the internal surface of top portion 12. Ribs 61 thus face the major axis of medial portion 22 so that when septum 20 is displaced laterally and distally when a male luer taper enters slit 25, ribs 61 engage septum 20 and hold septum 20 in housing 10. Because of its inherent resiliency, septum 20 can conform to the shape of ribs 61 and thus engage with and be held by ribs 61 until the male luer taper is removed from septum 20.

Figure 14:
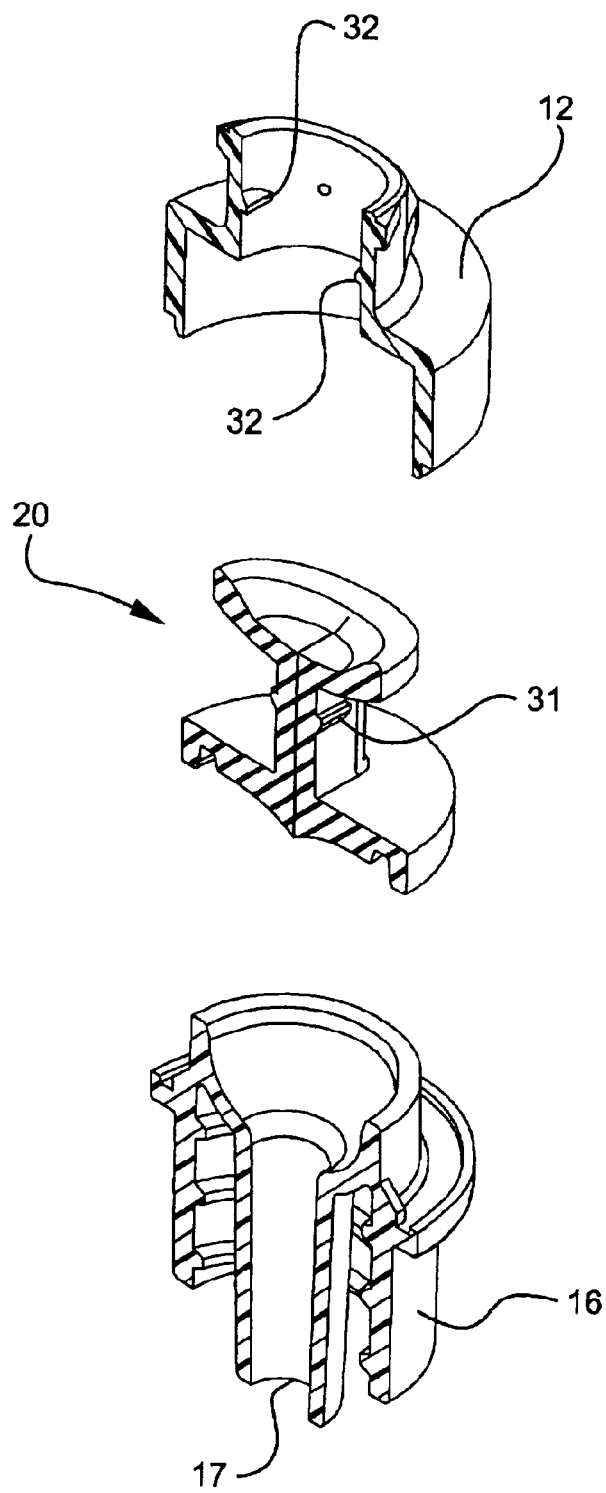
FIG. 14 is an exploded perspective view in cross section of the needleless luer access connector of this invention with a third embodiment of the septum and a fourth embodiment of the housing.
Figure 15:
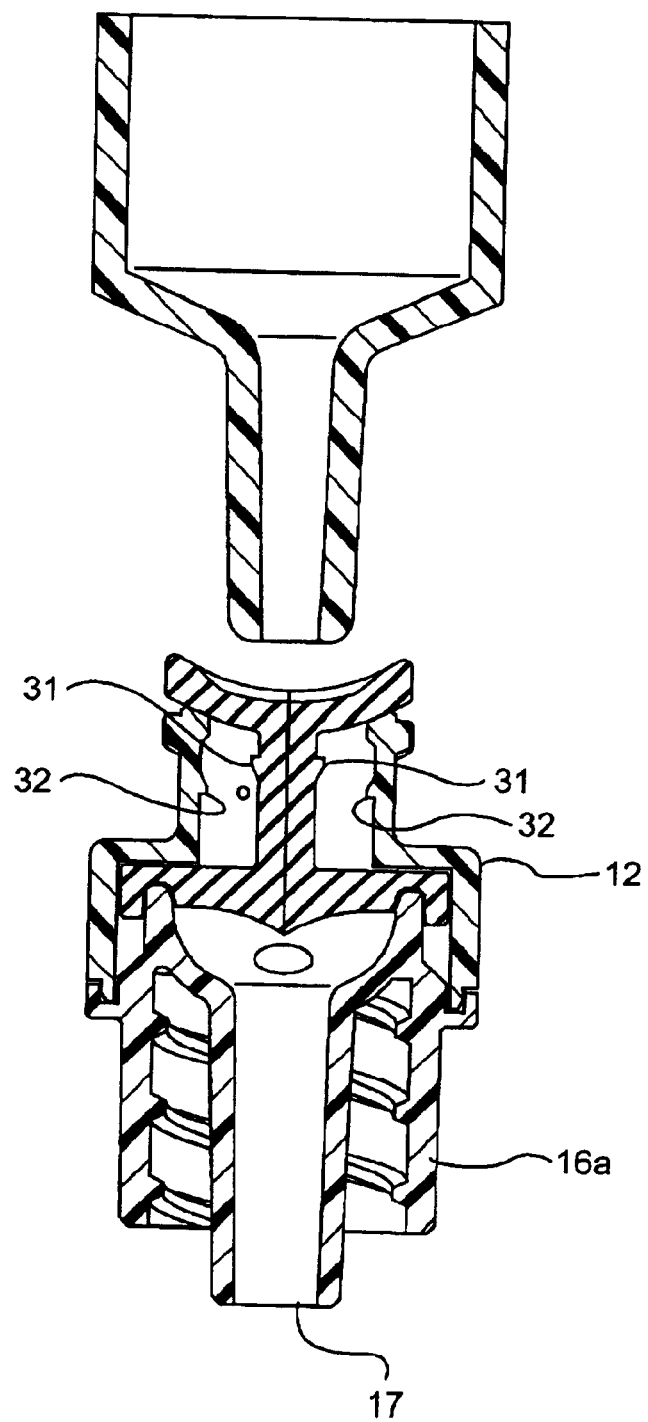
FIG. 15 is a cross sectional view of the needleless luer access connector of this invention with the third embodiment of the septum and the fourth embodiment of the housing with a male luer taper of another medical device such as a syringe poised for penetration of the connector.
Figure 16:
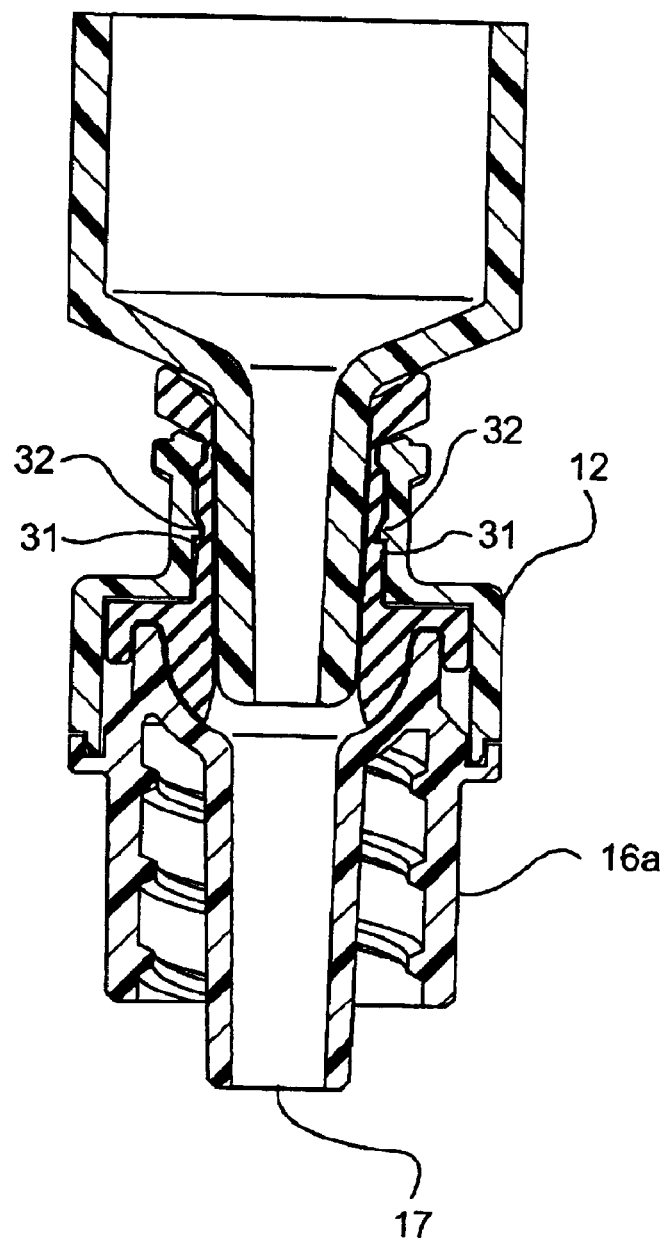
FIG. 16 is a cross sectional view of the needleless luer access connector of this invention with the third embodiment of the septum and the fourth embodiment of the housing with a male luer taper disposed therein.

The external surface of medial portion 22 of septum 20 may be formed with ribs 31 about 180 degrees apart along the major axis. In addition, complementary barbs 32 may be formed on the internal sidewalls of proximal portion 12 of housing 10 adjacent to inlet 11 and aligned with high points A. See FIGS. 14 through 16. Ribs 31 and barbs 32 are formed so as to engage with one another when brought into contact with each other. Thus, when the male luer taper of another medical device is fully inserted into septum 20, the external surface of medial portion 22 of septum 20 is forced distally and laterally so that it engages the internal sidewalls of proximal portion 12 of housing 10. Ribs 31 are located on septum 20 and barbs 32 are located on the internal sidewalls of top portion 12 of housing 10 so that when septum 20 is fully accessed by the male luer taper, ribs 31 engage barbs 32. Preferably, two ribs 31 are formed on septum 20 about 180 degrees apart along either side of medial portion 22 along the major axis thereof. Preferably two barbs 32 are located on the internal sidewalls of top portion 12 about 180 degrees apart and aligned with high points A so they are adjacent to ribs 31 when a male luer taper is inserted into septum 20. The longitudinal location of ribs 31 and barbs 32 can be determined by simple routine experimentation to see where a portion of septum 20 engages the internal sidewall of proximal portion 12. The interengagement of ribs 31 and barbs 32 helps to maintain septum 20 in place with respect to housing 10 as the male luer taper is being withdrawn from slit 25. This interengagement avoids the potential problem of septum 20 sticking to the male luer taper and being withdrawn from housing 10 as the male luer taper is withdrawn from housing 10. Since ribs 31 and barbs 32 interfere with and engage one another, the male luer taper can be removed from septum 20 without pulling septum 20 out of housing 10. However, the inherent resiliency of septum 20 allows ribs 31 and barbs 32 to disengage from each other once the male luer taper has been removed from septum 20 and thus allows septum 10 to return to its unbiased state.

Various configurations for ribs 31 and barbs 32 could be used to achieve this effect. For example, complementary ribs and detents or grooves could be formed on the exernal surface of medial portion 22 of septum 20 and the internal sidewalls of top portion 12. Barbs 32 can be formed anywhere along the axial length of top portion 12 but preferably barbs 32 are located close to top surface 15 and adjacent to inlet 11. This leaves a smaller portion of septum 20 above barbs 32 that may be pulled out of top portion 12 when the male luer taper is removed therefrom. If barbs 32 are located too far distally from top surface 15, a significant portion of septum 20 may be stretched and pulled out of top portion 12 if that portion of septum 20 sticks to the male luer taper.

Figure 17:
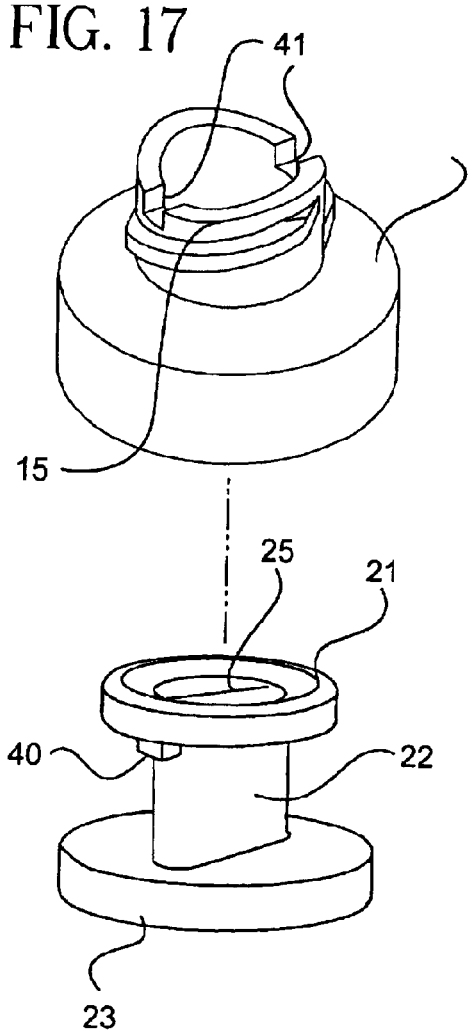
FIG. 17 is an exploded perspective view of a portion of the needleless luer access connector of this invention showing a fourth embodiment of the septum and a fifth embodiment of the housing.
Figure 18:
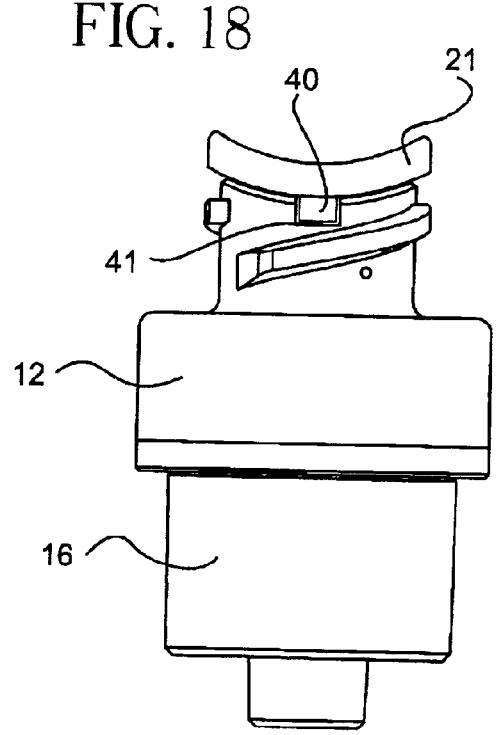
FIG. 18 is a side elevational view of the needleless luer access connector of this invention showing the fourth embodiment of the septum and the fifth embodiment of the housing.
Figure 19:
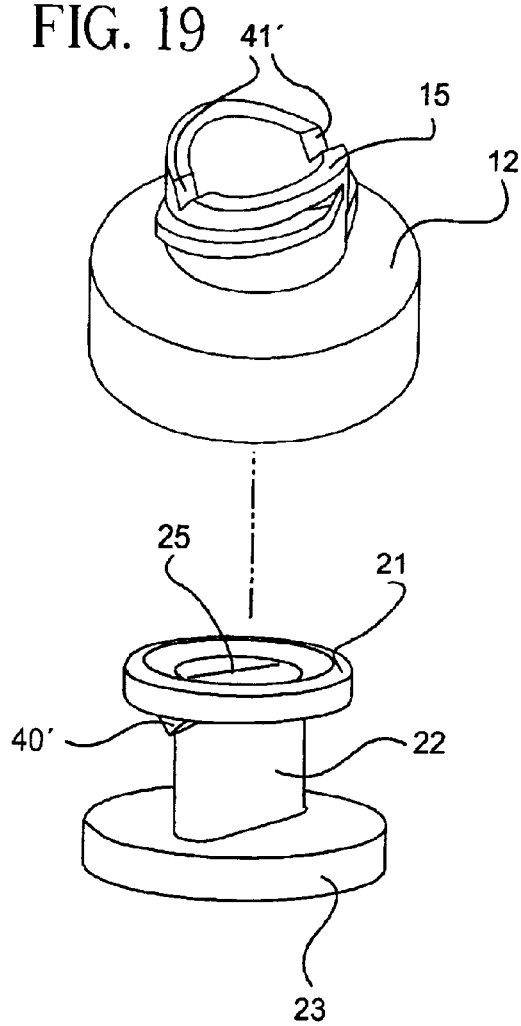
FIG. 19 is an exploded perspective view of a portion of the needleless luer access connector of this invention showing a fifth embodiment of the septum and a sixth embodiment of the housing.
Figure 20:
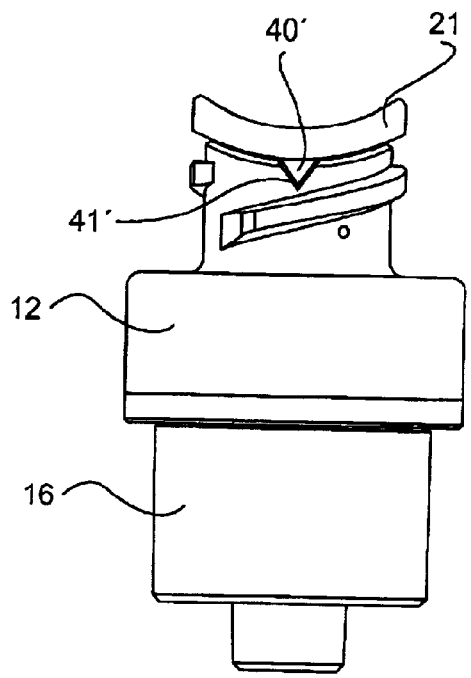
FIG. 20 is a side elevational view of the needleless luer access connector of this invention showing the fifth embodiment of the septum and the sixth embodiment of the housing.
Figure 21:
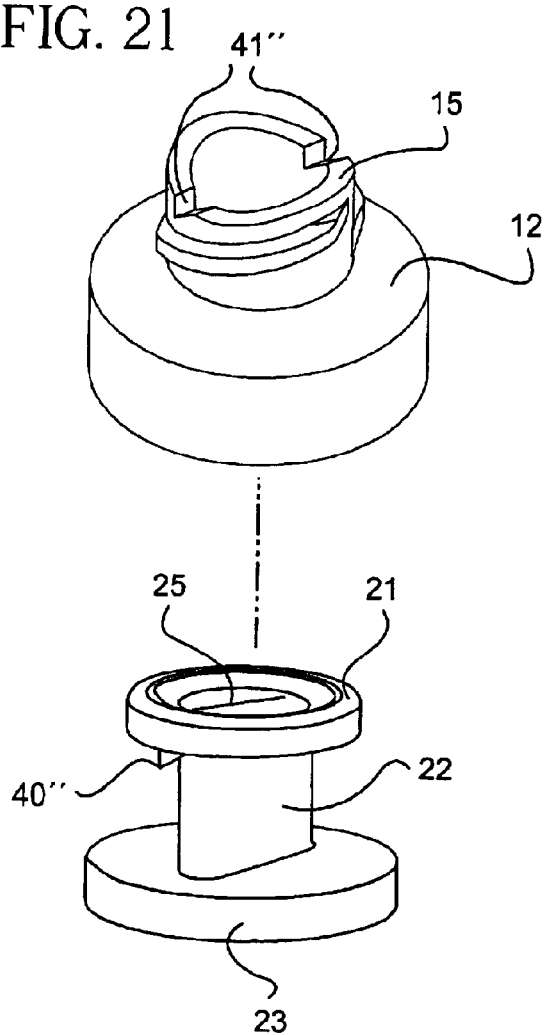
FIG. 21 is an exploded perspective view of a portion of the needleless luer access connector of this invention showing a sixth embodiment of the septum and the seventh embodiment of the housing.
Figure 22:
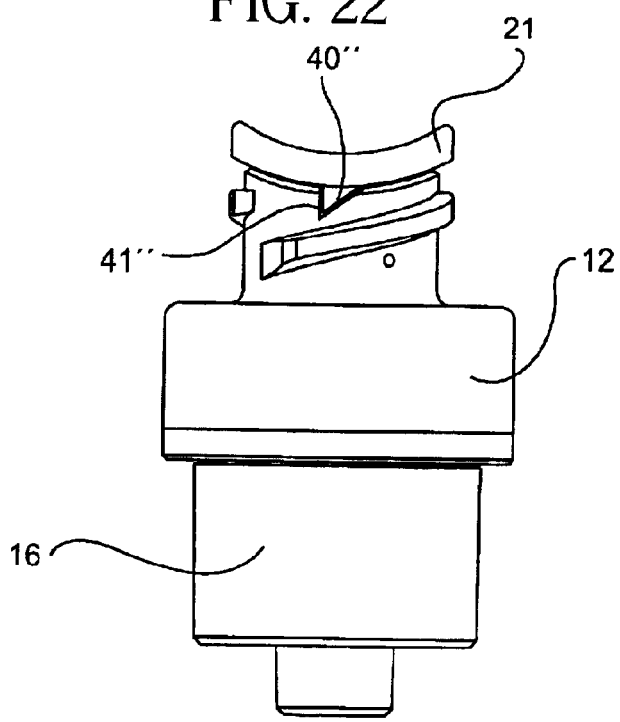
FIG. 22 is a side elevational view of the needleless luer access connector of this invention showing the sixth embodiment of the septum and the seventh embodiment of the housing.
Figure 25:
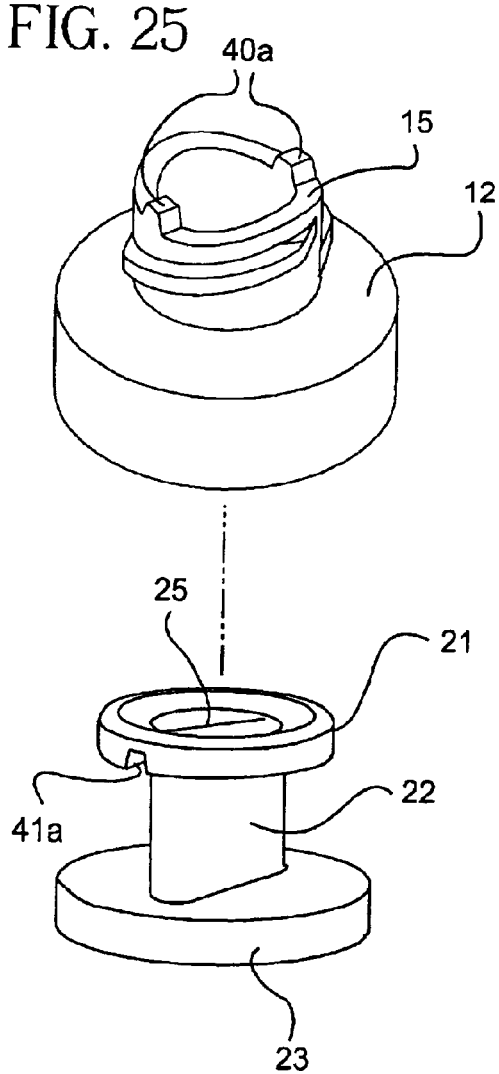
FIG. 25 is an exploded perspective view of a portion of the needleless luer access connector of this invention showing an eighth embodiment of the septum and a ninth embodiment of the housing.
Figure 26:
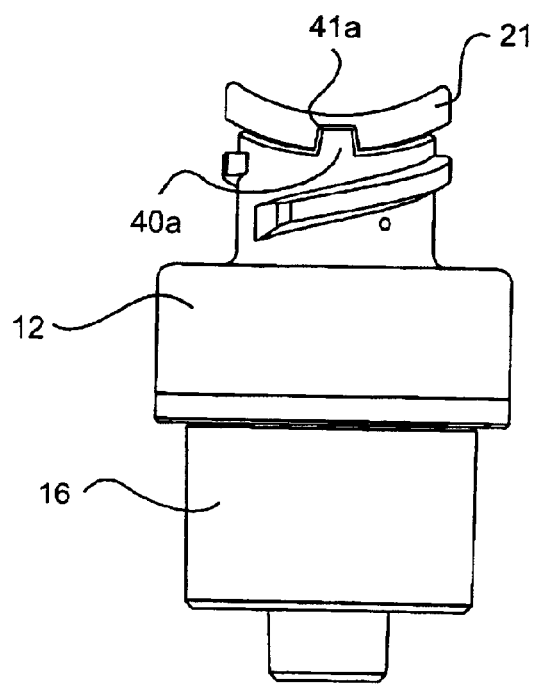
FIG. 26 is a side elevational view of the needleless luer access connector of this invention showing the eighth embodiment of the septum and the ninth embodiment of the housing.

A variation of the foregoing feature is the use of various key and key hole configurations formed on septum 20 and top portion 12 to prevent rotation of septum 20 during insertion of a male luer taper into septum 20 or removal of a male luer taper from septum 20. See FIGS. 17 through 28. This may be necessary, especially where inlet 11 is configured for a male luer lock. In such a case the male luer taper of another medical device is typically rotated with respect to housing 10 of the needleless luer access connector of this invention to insert the male luer taper into the connector and lock it in place and to unlock the male luer taper and remove it from the connector. For example, a key 40 could be formed on septum 20 adjacent to enlarged proximal portion 21 of septum 20 along the minor axis of medial portion 22 and aligned with, i.e. collinear or parallel, transverse axis T of slit 25 and the major axis of medial portion 22. Key 40 could merely be an extension from one side of septum 20 and can be formed in any shape. For example, a simple rectangular shape, see FIGS. 17 and 18, could be used as well as a triangular, see FIGS. 19 through 22, or other polygonal shape, see FIGS. 23 and 24, could be used.

Preferably, two keys 40 are used and are located about 180 degrees apart and aligned with transverse axis T and the major axis of medial portion 22. A complementary slot or keyhole 41 could be formed along adjacent to top surface 15 at top portion 12 of housing 10. Preferably, two keyholes 41 are used and are located about 180 degrees apart aligned with the low points B. Keys 40 need not extend to the periphery of enlarged proximal portion 21 and keyholes 41 need not extend completely through the sidewall of top portion 12. Instead, keys 40 could be formed as a rib extending from medial portion 22 and keyholes 41 could be formed as complementary grooves formed in the internal sidewall of top portion 12. The only limitation is that keys 40 and keyholes 41 must be configured and located with respect to each other so that they combine to hold septum 20 against rotational movement with respect to housing 10. Moreover, keys 40a could be formed along top surface 15 of top portion 12 of housing 10 and keyholes 41a can be formed in septum 20 adjacent to proximal portion 21. See FIGS. 25 thorugh 28. Preferably two keys 40a and two keyholes 41a are used with keys 40a about 180 degrees apart and keyholes 41a about 180 degrees apart. Keys 40a or keyholes 41a can be located anywhere about the circumference of proximal portion 21. However, preferably keys 40a are aligned with low points B and keyholes 41a are aligned with the major axis of medial portion 22 and transverse axis T of slit 25. Although the embodiments of FIGS. 17 through 28 preferably have a top surface 15 with high points A and low points B, the keys and keyholes of these embodiments could be used where the needleless luer access connector of this invention has a flat top surface 15 with no high or low points.

Figure 29:
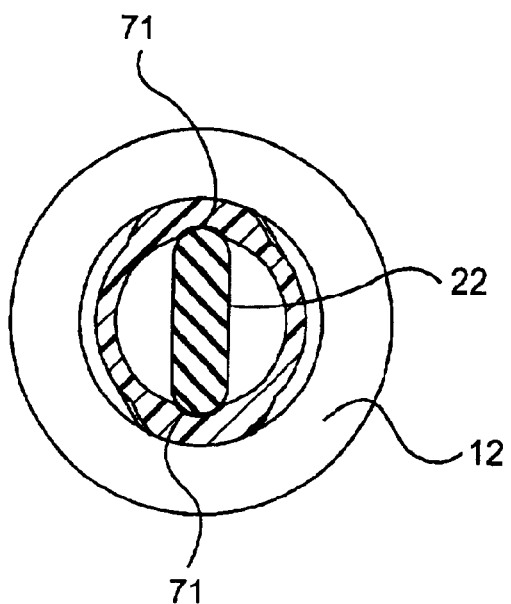
FIG. 29 is a top plan view in cross section of the needleless luer access connector of this invention taken along line 29—29 of FIG. 4 showing an eleventh embodiment of the housing.
Figure 30:
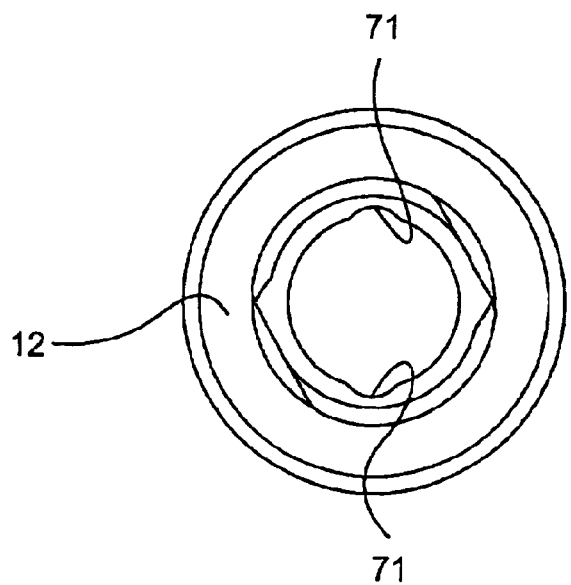
FIG. 30 is a top plan view of the eleventh embodiment of housing with the septum removed from the housing.
Figure 31:
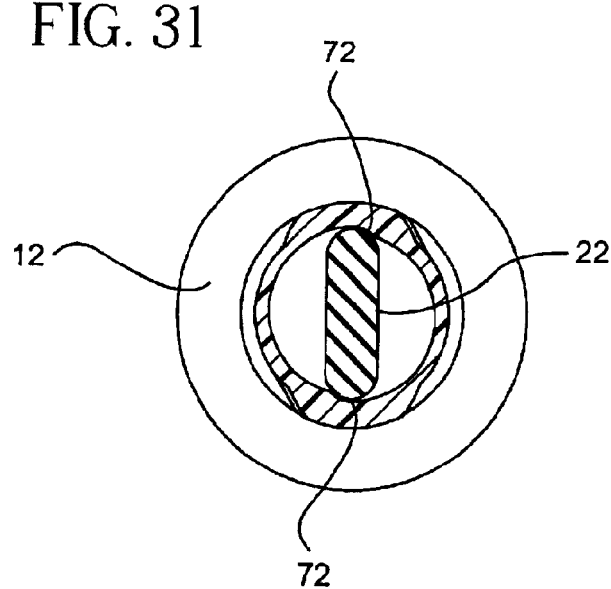
FIG. 31 is a top plan view in cross section of the needleless luer access connector of this invention similar to the view of FIG. 29 but showing a twelfth embodiment of the housing.
Figure 32:
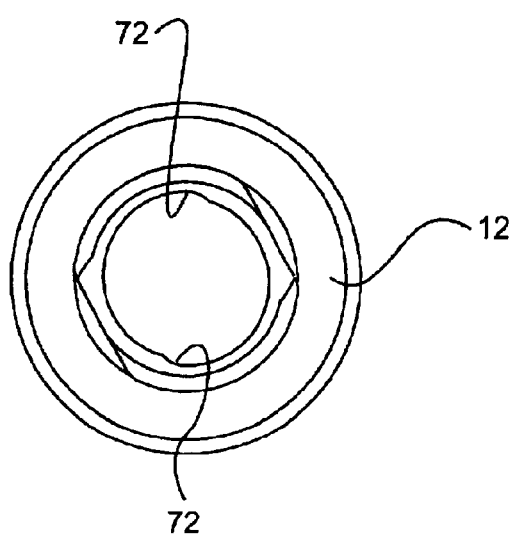
FIG. 32 is a top plan view of the twelfth embodiment of the housing with the septum removed from the housing.
Figure 33:
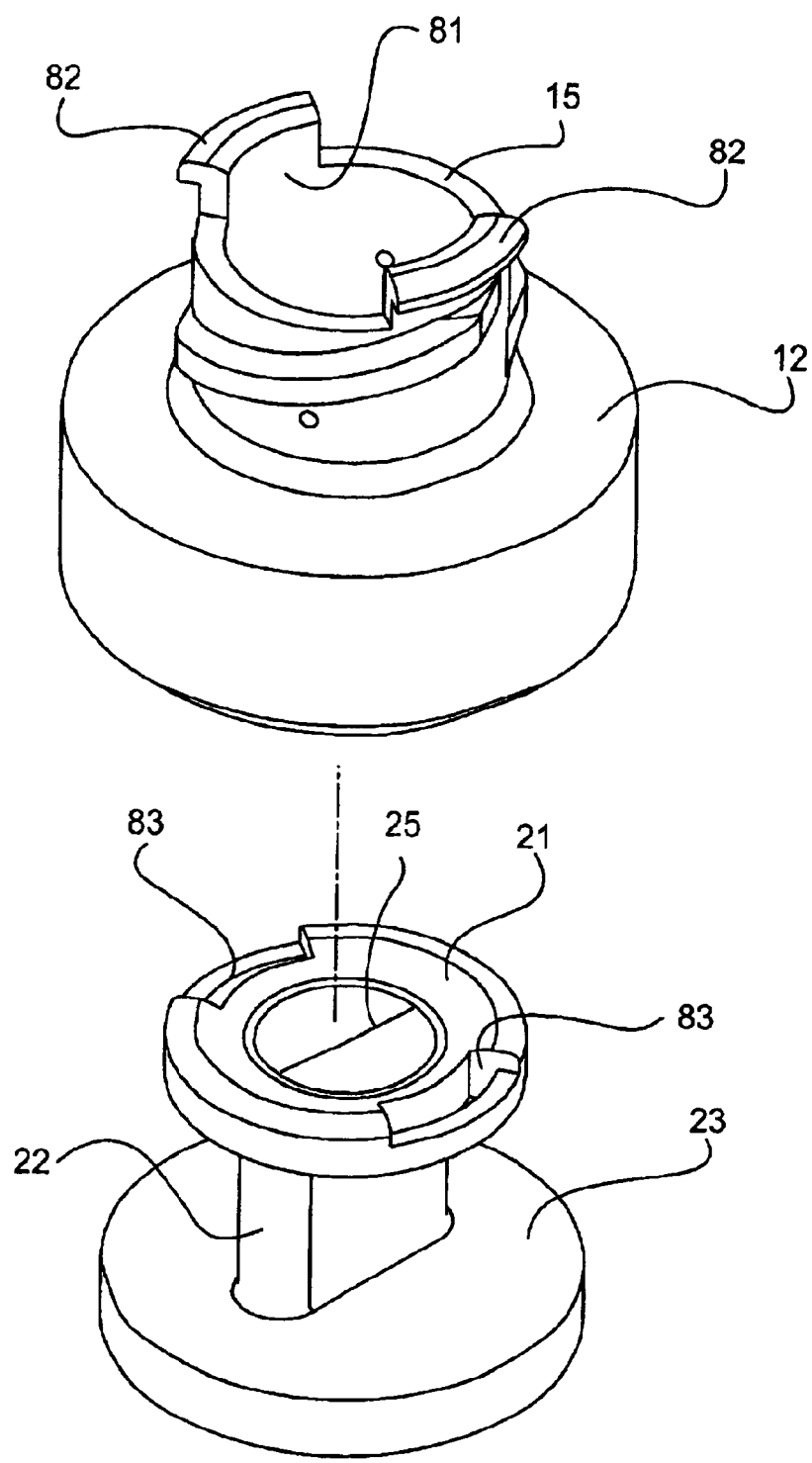
FIG. 33 is an exploded perspective view of a portion of the needleless luer access connector of this invention showing a tenth embodiment of the septum and a thirteenth embodiment of the housing.
Figure 34:
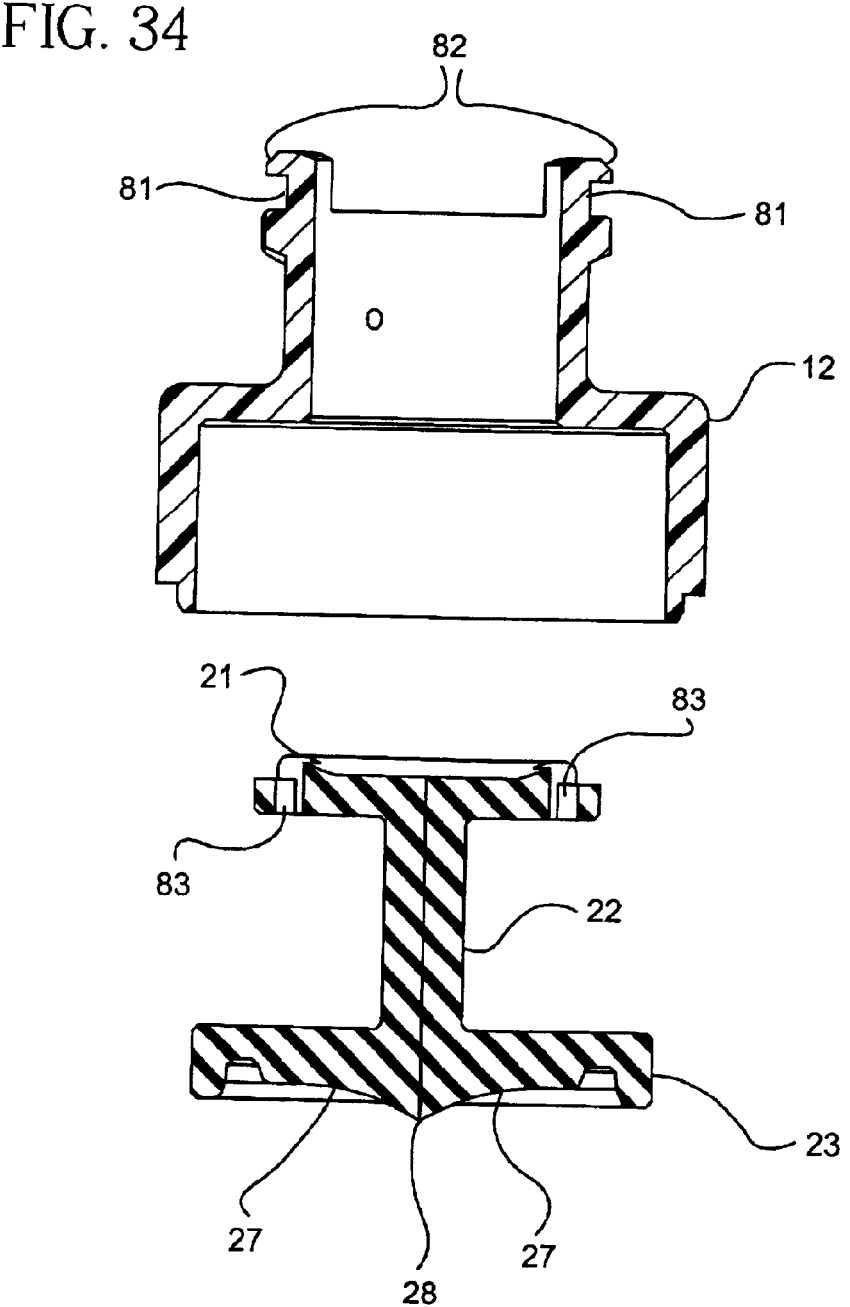
FIG. 34 is an exploded cross sectional view of a portion of the needleless luer access connector of this invention showing the tenth embodiment of the septum and the thirteenth embodiment of the housing.
Figure 35:
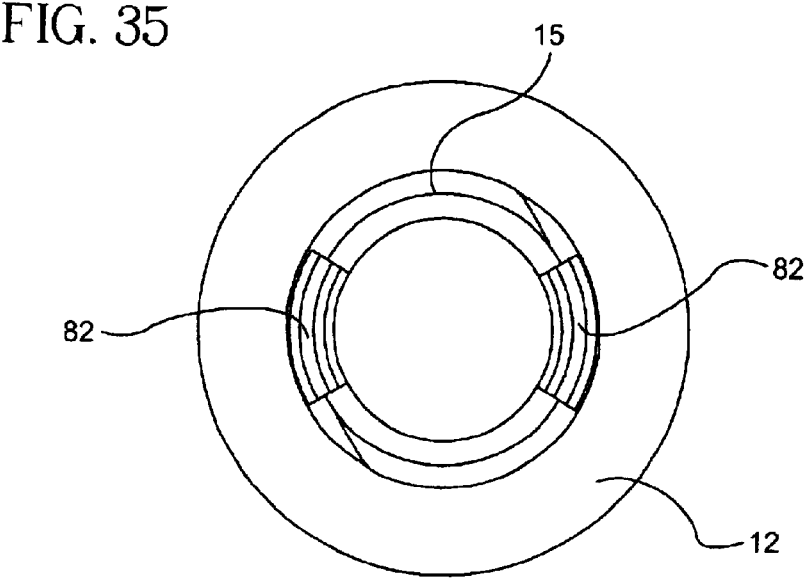
FIG. 35 is a top plan view of the thirteenth embodiment of the housing of the needleless luer access connector of this invention.
Figure 36:
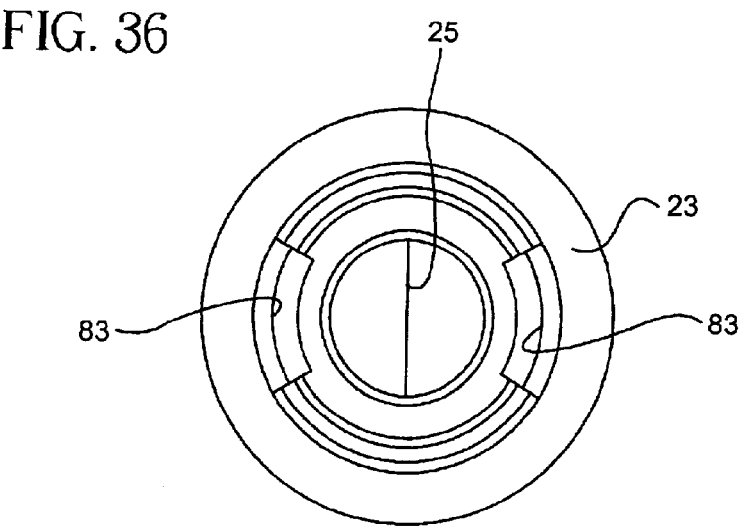
FIG. 36 is a top plan view of the tenth embodiment of the septum of the needleless luer access connector of this invention.

Bore 13 could be formed with a longitudinally extending groove 71 that engages the ends of medial portion 22. See FIGS. 29 and 30. Preferably, two grooves 71 are used and each groove 71 is preferably about 180 degrees apart and substantially aligned with the low points B. In this manner each end of medial portion 22 parallel to the minor axis engages grooves 71 to hold septum 20 against rotation with respect to bore 13. Alternatively, bore 13 could be formed with two shoulders 72 therein that engage the ends of medial portion 22. See FIGS. 31 and 32. Again, preferably two shoulders 72 are used and each shoulder 72 is preferably about 180 degrees apart and substantially aligned with the low points B. These configurations for bore 13 help to hold medial portion 22, and thus septum 20, in place against rotation with respect to housing 10 where a male luer taper is inserted or removed from septum 20 by twisting the male luer taper.

Since proximal portion 21 of septum 20 merely rests on top surface 15 of top portion 12 of housing 10, it is possible that proximal portion 21 could be forced into bore 13 of top portion 12 when a male luer taper is pressed against the top of proximal portion 21. A configuration for septum 20 and housing 10 that helps to hold proximal portion 21 in place when a male luer taper is forced into slit 25 is shown in FIGS. 33 through 36. In this embodiment, risers 81 are formed in top portion 12 adjacent to and extend up from top surface 15 and are about 180 degrees apart. Risers 81 include outwardly extending flanges 82 thereon. Slotted portions 83 are formed along the periphery of proximal portion 21 and allow flanges 82 to extend into and through slotted portions 83. Preferably two slotted portions 83 about 180 degrees apart are formed on proximal portion 21 and extend generally parallel to transverse axis T of slit 25 on either side thereof. If desired, a barb can be formed on risers 81 or flange 82 to engage slotted portions 83 and help hold slotted portions 83 in place with respect to top surface 15. This engagement also helps to hold proximal portion 21 in place when a male luer taper is forced into slit 25. Preferably, top surface 15 is flat in this embodiment. However, if desired, top surface 15 may be formed with an undulating curved surface with two high points and two low points as in the other embodiments. If such an undulating surface were used, risers 81 would include the high points.

Figure 38:
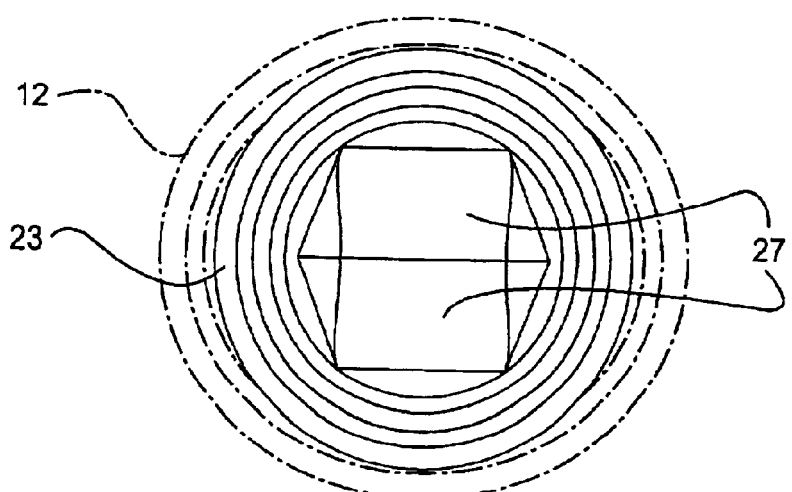
FIG. 38 is a bottom plan view of the distal portion of the septum having a circular cross section and showing in phantom that portion of the housing engaging the distal portion of the septum with an elliptical cross section to provide a comparison between the two.

In order to facilitate the closing of slit 25 against fluid flow, the portion of housing 10 that engages distal portion 23 of septum 20 can be configured so that housing 10 compresses distal portion 23 of septum 20 along the sides of slit 25. Alternatively or concurrently, the portion of housing 10 that engages distal portion 23 of septum 20 can be configured so housing 10 pulls distal portion 23 of septum 20 in tension at the ends of slit 25, i.e. along transverse axis T. One way to achieve this force distribution, is for distal portion 23 of septum 20 to be formed with a substantially circular cross section while the portion 12 of housing 10 that engages distal portion 23 is formed with a substantially elliptical or oval cross section. See FIG. 38. By locating slit 25 so that transverse axis T is parallel to the major axis of the ellipse, slit 25 will be biased to a closed position. This is because the minor axis of the ellipse will tend to compress sides 25a of slit 25 together while the major axis of the ellipse will tend to pull ends 25b of slit 25 in tension thus forcing slit 25 closed. As noted above, either tension along slit 25 or compression perpendicular to slit 25 can be applied and not necessarily both. Only tension can be achieved by forming the minor axis of the ellipse so that it is substantially equal to the diameter of the circular cross section of distal portion 23 and forming the major axis of the ellipse so that it is greater than the diameter. Only compression can be achieved by forming the minor axis of the ellipse so that it is smaller than the diameter and forming the major axis of the ellipse so that it is substantially equal to the diameter. This effect can also be achieved by forming complementary tabs and slots in distal portion 23 of septum 20 and the portion of housing 10 that engages distal portion 23 to pull and push distal portion 23 in the appropriate directions as described above.

Figure 37:
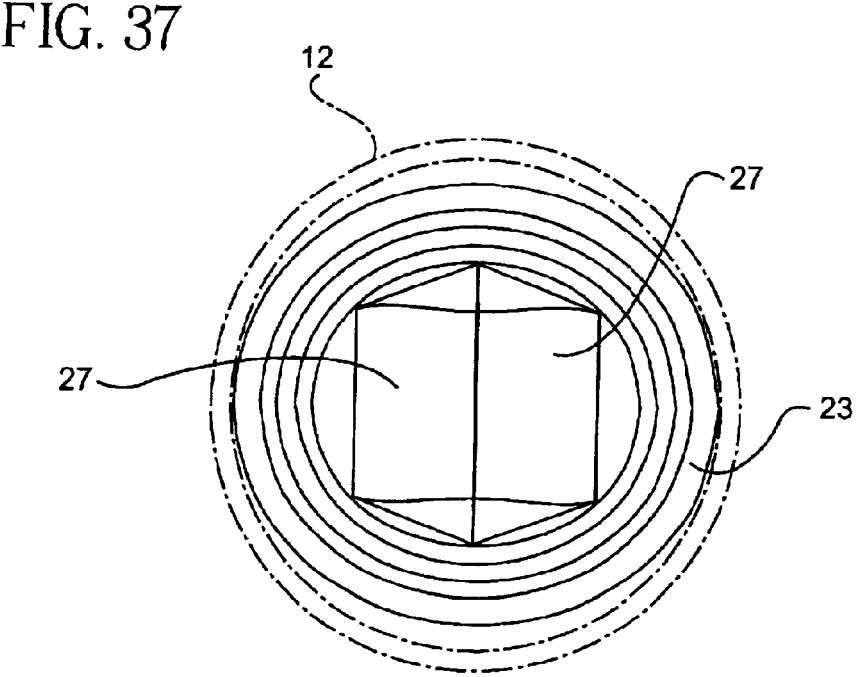
FIG. 37 is a bottom plan view of the distal portion of the septum having an elliptical cross section and showing in phantom that portion of the housing engaging the distal portion of the septum with a circular cross section to provide a comparison between the two.
Figure 39:
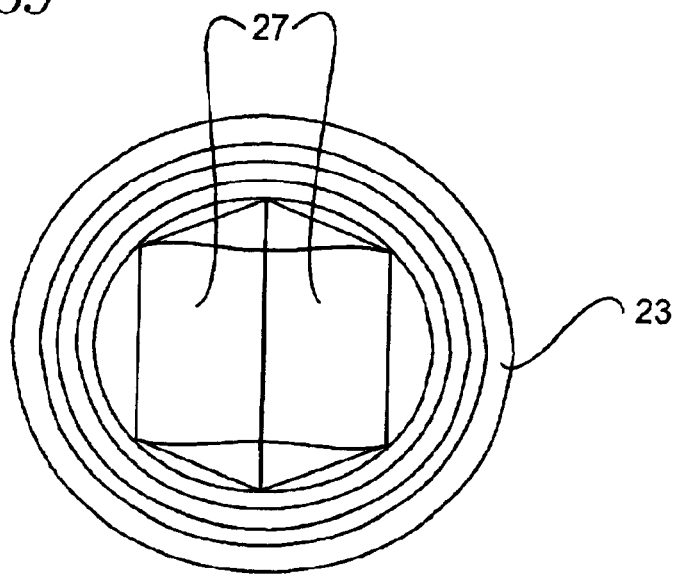
FIG. 39 is a bottom plan view of the distal portion of the septum having an elliptical cross section.
Figure 40:
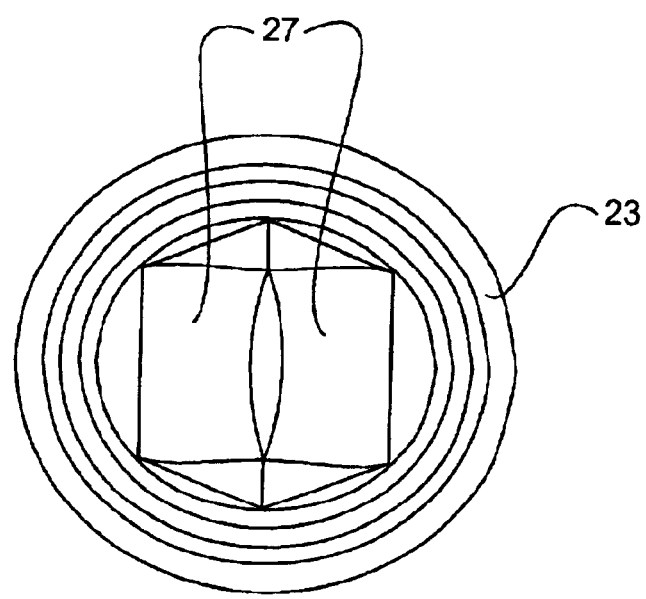
FIG. 40 is a bottom plan view of the distal portion of the septum having an elliptical cross section with a slit having a molded open configuration.
Figure 41:
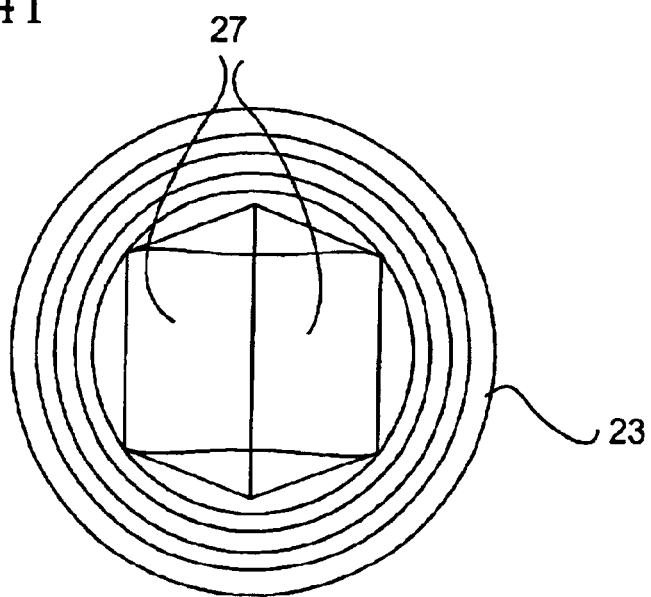
FIG. 41 is a bottom plan view of the distal portion of the septum having a circular cross section.
Figure 42:
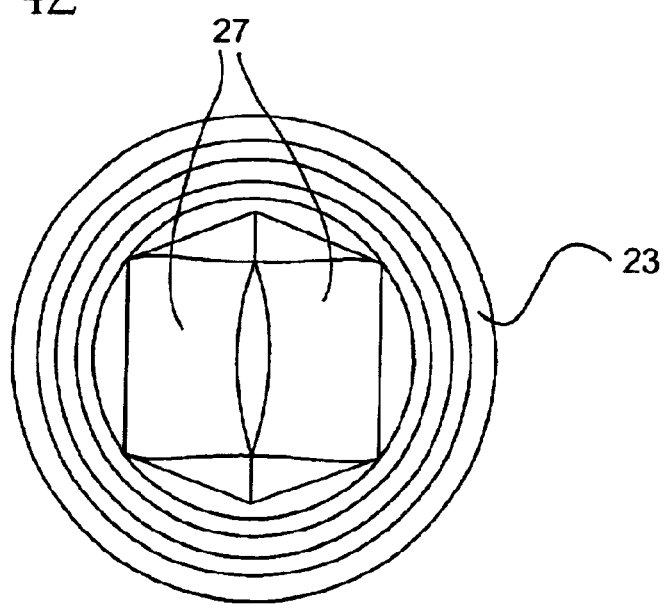
FIG. 42 is a bottom plan view of the distal portion of the septum having a circular cross section with a slit having a molded open configuration.
Figure 43:
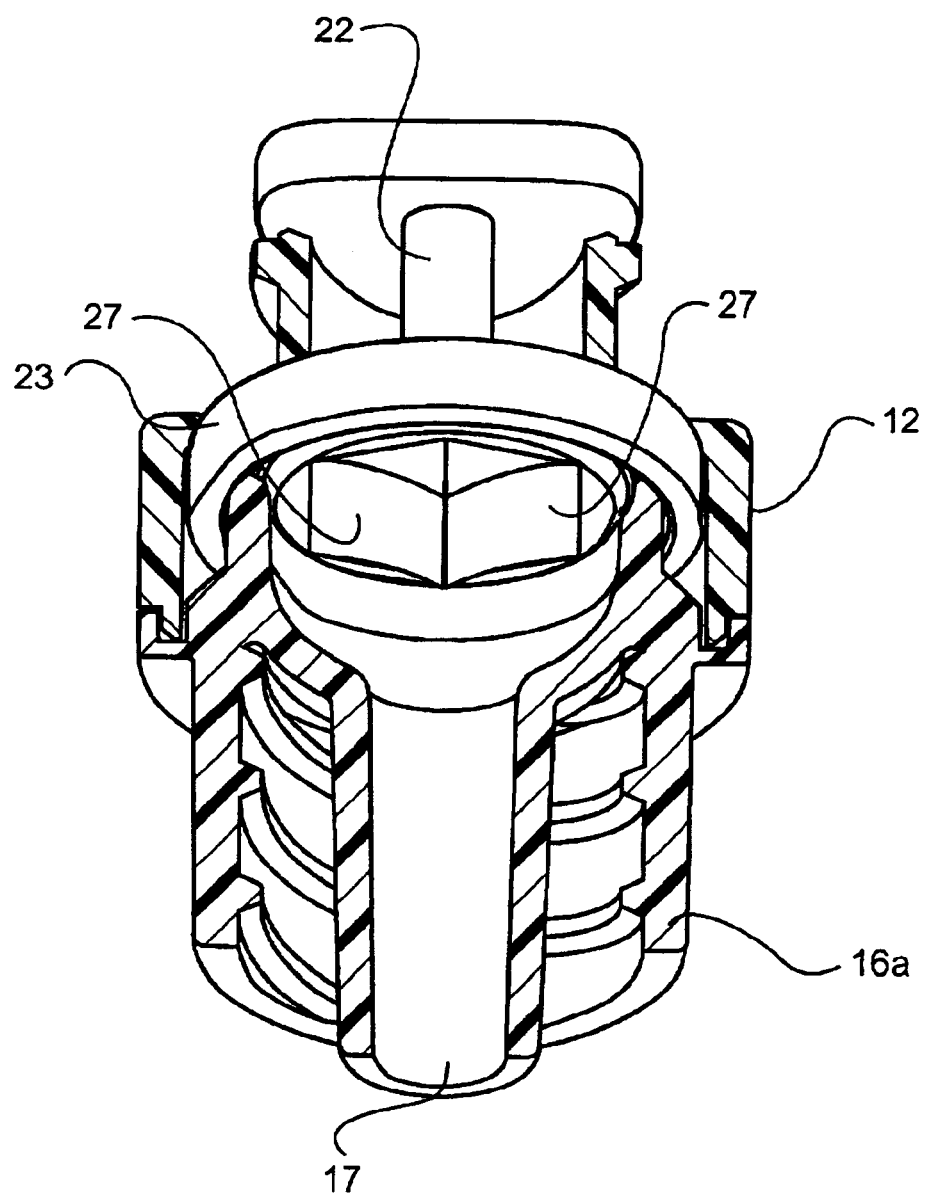
FIG. 43 is a bottom perspective view partially in cross section of the needleless luer access connector of this invention showing the distal portion of the septum and that portion of the housing that engages the distal portion of the septum.
Figure 44:
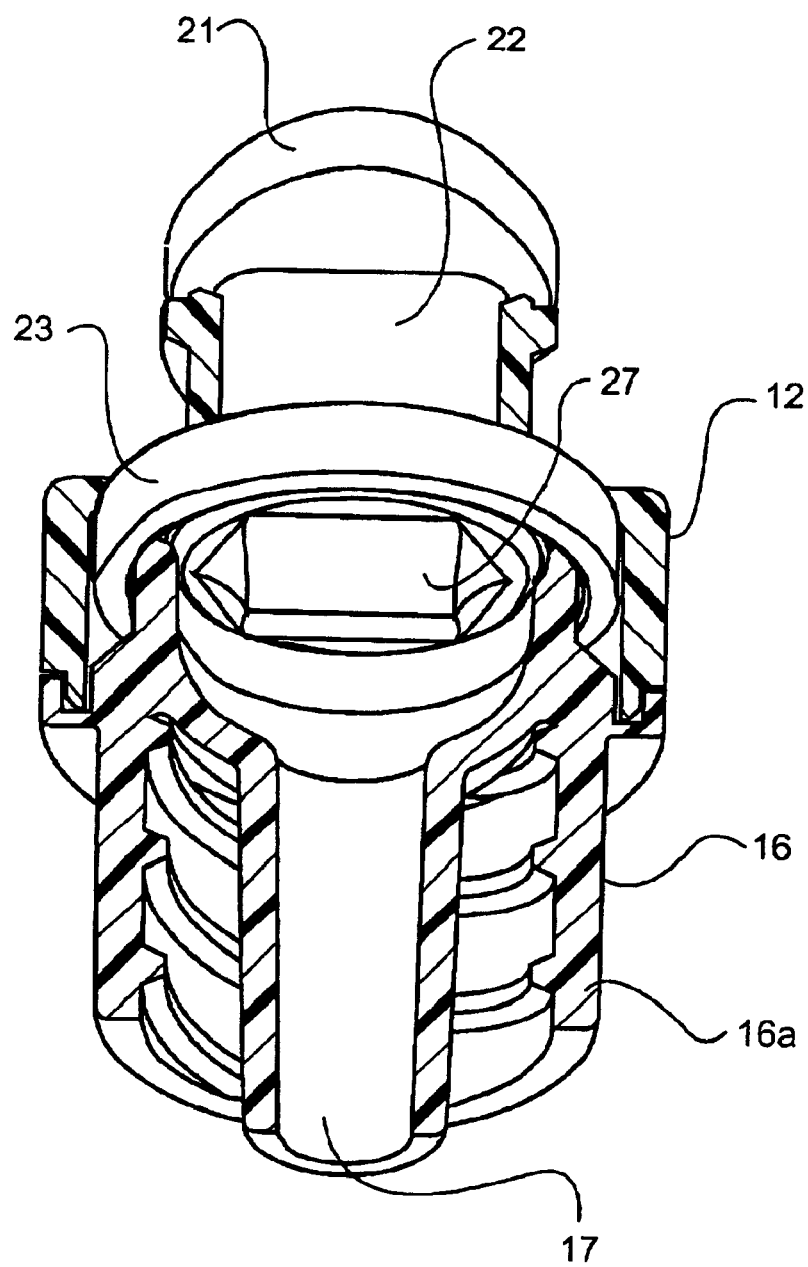
FIG. 44 is a bottom perspective view partially in cross section of the needleless luer access connector of this invention showing the distal portion of the septum and that portion of the housing that engages the distal portion of the septum rotated 90 degrees from the view of FIG. 43.
Figure 45:
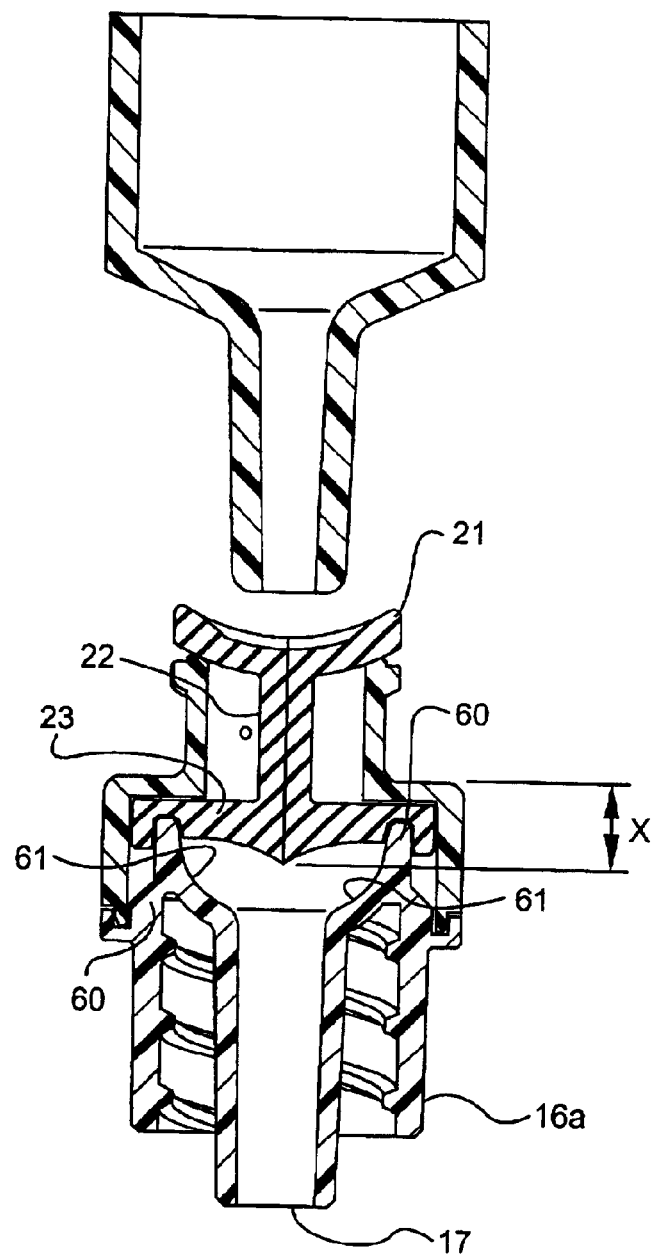
FIG. 45 is a cross sectional view of the needleless luer access connector of this invention closed to fluid flow and a male luer taper of another medical device such as a syringe poised for penetration of the connector.
Figure 46:
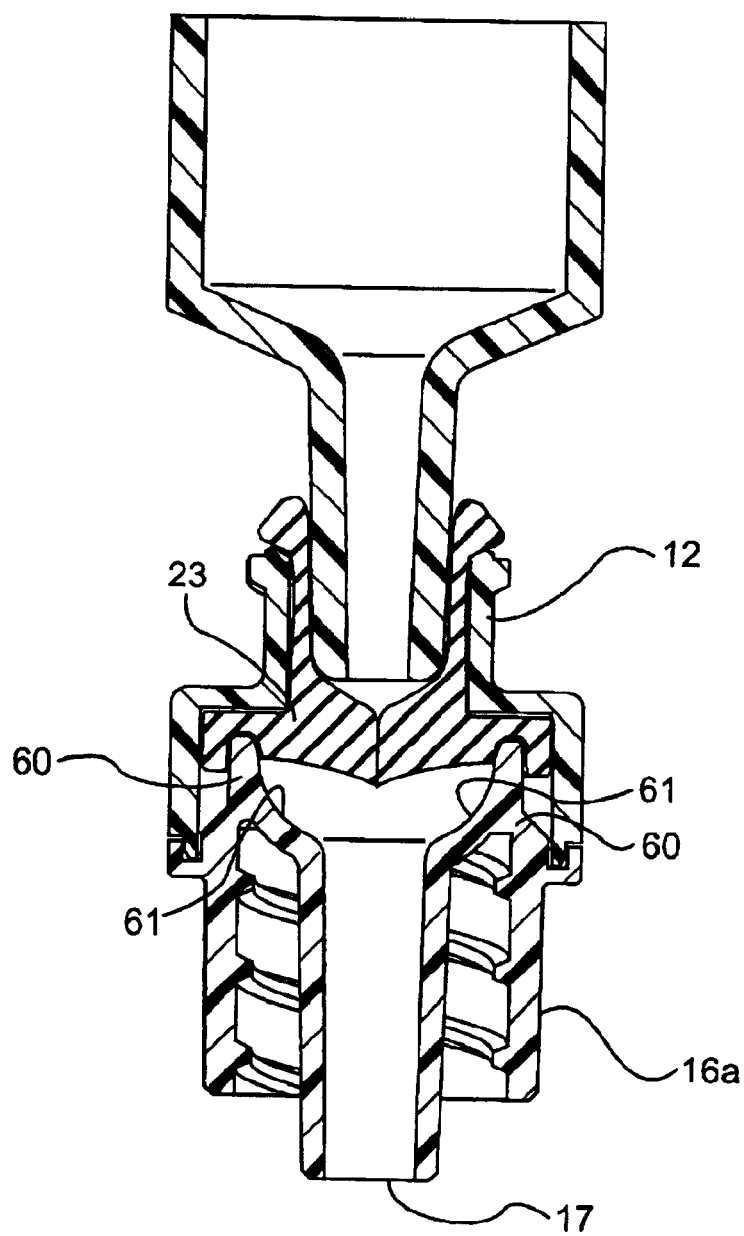
FIG. 46 is a cross sectional view of the needleless luer access connector of this invention with a male luer taper of another medical device such as a syringe disposed in the septum in the connector but with the connector still closed to fluid flow.
Figure 47:
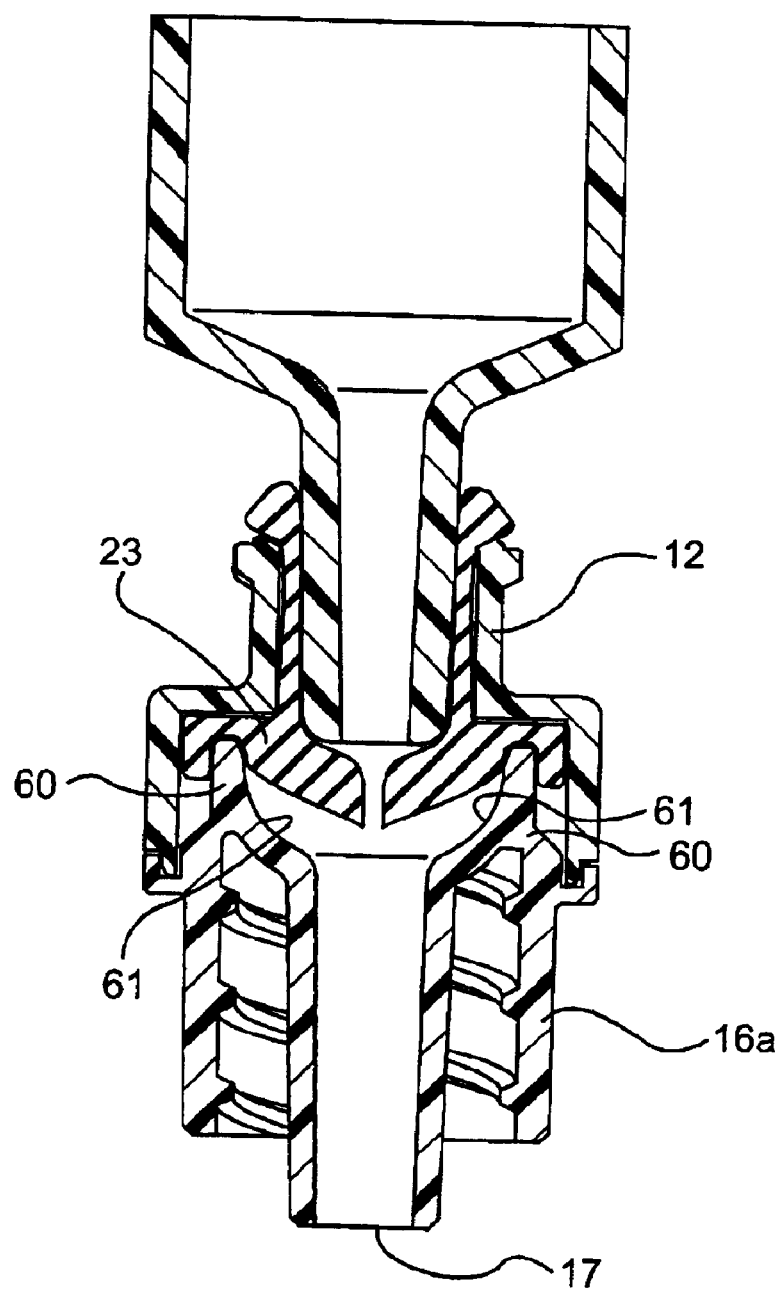
FIG. 47 is a cross sectional view of the needleless luer access connector of this invention with a male luer taper of another medical device such as a syringe disposed further in the connector but with the distal end of the male luer taper proximal of the distal end of the septum but with the connector open to fluid flow.

Alternatively and preferably, distal portion 23 of septum 20 is formed in an elliptical configuration and the portion of housing 10 that engages distal portion 23 is formed with a circular cross section. See FIG. 37. When distal portion 23 has an elliptical configuration transverse axis T of slit 25 is preferably aligned with, i.e. collinear, with the minor axis of the ellipse. This configuration for distal portion 23 and that portion of housing 10 that engages distal portion 23 facilitates manufacturing of the needleless access connector of this invention because it does not require special alignment between distal portion 23 and housing 10. Only tension can be achieved by forming the minor axis of the ellipse so that it is less than the diameter of the circular cross section of distal portion 23 and forming the major axis of the ellipse so that it is substantially equal to the diameter. Only compression can be achieved by forming the minor axis of the ellipse so that it is substantially equal to the diameter and forming the major axis of the ellipse so that it is greater than the diameter. Preferably, with this configuration, the minor axis of distal portion 23 is about 0.360 inches (9.144 millimeters) and the major axis of distal portion 23 is about 0.430 inches (10.922 millimeters) when distal portion 23 is in its unstressed state. If desired, slit 25 can be formed so it is open when distal portion 23 is in its unstressed state. In this situation, slit 25 has an elliptical cross section at distal portion 23 with a minor axis of about 0.030 inches (0.762 millimeters) and a major axis of about 0.175 inches (4.445 millimeters) and distal portion 23 has a minor axis of about 0.360 inches (9.144 millimeters) and a major axis of about 0.460 inches (11.684 millimeters). See FIG. 40. Of course, septum 20 can be formed with a circular cross section at distal portion 23 and an open slit 25. See FIG. 42. Alternatively, septum 20 can be formed with an elliptical cross section at distal portion 23 with a closed slit 25, see FIG. 39, or a circular cross section at distal portion and a closed slit 25, see FIG. 41.

When a male luer taper is pushed against the top proximal surface of septum 20, proximal portion 21 deflects distally and laterally and allows the male luer taper to access slit 25 in septum 20. As the male luer taper is pushed further into slit 25, medial portion 22 also deflects distally and laterally. By having a cross-section for medial portion 22 that is smaller than the cross-section of bore 13, space is provided in housing 10 to allow such lateral deflection of medial portion 22. This distal and lateral deflection of septum 20 forces slit 25 to open and allows the male luer taper to penetrate septum 20 through slit 25. When the male luer taper is fully inserted into septum 20, slit 25 is forced open along the entire length of septum 20.

Because of certain ISO standards, it is important that slit 25 is open along the entire length of septum 20 even if the male luer taper does not extend completely through septum 20. For male luer locks, ISO standard 594-2:1998(E) requires that the male luer taper have a minimum length of about 0.295 inches (7.5 millimeters) and extend a minimum of 0.083 inches (2.1 millimeters) past the end of the luer lock collar. Many manufacturers make their products with this minimum dimension. In the needleless access connector of this invention, the distance X between the top of the medial sidewall of proximal portion 12 and the bottom of septum 20 is about 0.110 inches (2.794 millimeters). Thus it can be seen that where a male luer taper having the minimum ISO dimensions is used to access the needleless access connector of this invention, the male luer taper will not extend completely through septum 20. Because of these dimensions, septum 20 must be designed so that slit 25 is forced open even if the male luer taper does not extend completely through septum 20. When a male luer taper is inserted into septum 20 a distance of about 0.214 inches (5.436 millimeters) from the top of septum 20, the bottom of slit 25 begins to open. When the male luer taper is inserted as far as it can extend into the needleless access connector, distal portion 23 can only be deflected distally down into bore 13 below where the bottom of distal portion 23 extends when it is not accessed by a male luer taper. This distal deflection causes distal portion 23 to act as a swinging door and fully open slit 25. There is only distal deflection of distal portion 23 because the circumference of distal portion 23 is held in place between proximal portion 12 and distal portion 16 of housing 10 and there is no room for distal portion 23 to move except distally. In addition, distal portion 23 has an increased mass by virtue of its thickness, which is about 0.050 inches (1.27 millimeters) and which tapers up to about 0.080 inches (2.032 millimeters) immediately adjacent to slit 25. This combination of holding distal portion 23 against lateral movement and the increased mass of distal portion forces slit 25 open and allows fluid to flow through the needleless luer access connector even if the male luer taper does not completely penetrate septum 20.

Figure 48:
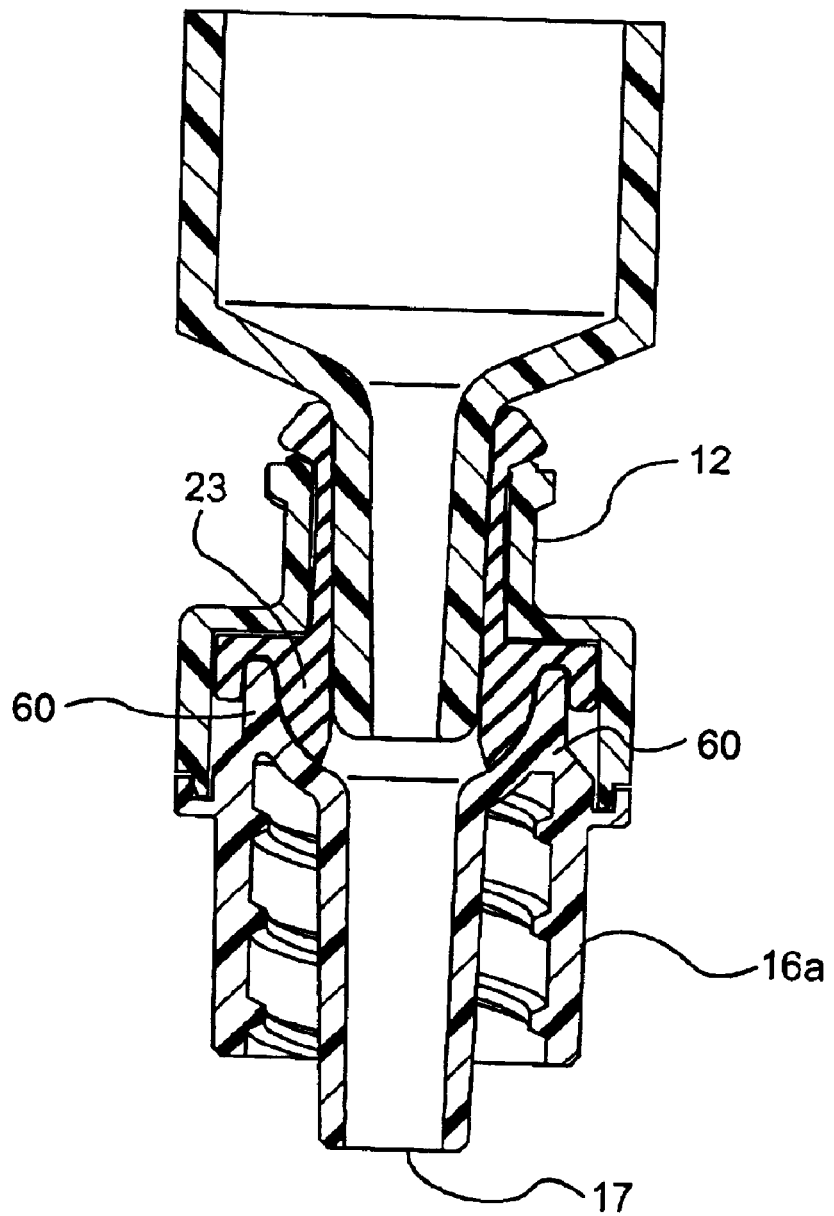
FIG. 48 is a cross sectional view of the needleless luer access connector of this invention with a male luer taper of another medical device such as a syringe disposed as far as it can go in the connector but with the distal end of the male luer taper proximal of the distal end of the septum and with the connector open to fluid flow.

Housing 10 is designed to minimize the amount of any dead space therein where fluid could flow and be trapped. Any such trapped fluid can provide a breeding ground for microbes and other organisms that could travel through the needleless luer access connector and into the patient to infect the patient. Preferably, walls 60 are formed in distal portion 16 of housing 10 to fill any dead space therein. Walls 60 have an upwardly facing surface 61 that matches the configuration of distal portion 23 of septum 20 when a male luer taper fully accesses the needleless luer access connector of this invention. See FIG. 48. In this way, walls 60 do not interfere with the normal operation of the invention while still filling any unused space within housing 10.

Thus, it is seen that a needleless access connector is provided that can be accessed with the use of a needle, that is not prone to leakage or microbial ingress, that minimizes the dead space volume therein, that does not require a high degree of force to access and minimizes the kickback force when the connector is accessed and that does not require any additional or special devices to access.

We claim:

1. A needleless luer access connector, comprising:

a housing having a top portion defining an inlet opening, a channel defined by at least one sidewall extending from the inlet opening and having a cross section, and a bottom portion defining an outlet opening extending from the channel;

a barb formed along the sidewall of the channel and extending into the channel;

a septum disposed in the housing, the septum having a proximal portion, a medial portion having an external surface and a cross section less than a cross section of the top portion and less than the cross section of the channel and a distal portion;

a longitudinal slit extending through the septum from the proximal portion through the medial portion and into the distal portion; and at least one rib formed on the external surface of the medial portion such that the rib is displaced from the barb until a male luer taper is inserted into the slit, at which point the rib engages the barb.

2. The needleless luer access connector of claim 1 wherein the longitudinal slit is defined by a pair of transversely extending walls of the septum and the external surface of the medial portion includes at least one portion that is substantially aligned with at least one of the transversely extending walls of the septum and the at least one rib is located on the at least one portion.

3. The needleless luer access connector of claim 2 wherein the external surface of the medial portion includes two portions, each of which is substantially parallel to the pair of transversely extending walls of the septum.

4. The needleless luer access connector of claim 3 including two ribs wherein one rib is located on each of the two portions of the external surface of the medial portion.

5. The needleless luer access connector of claim 4 further including two barbs on the sidewall of the channel.

6. The needleless luer access connector of claim 5 wherein the two barbs are about 180 degrees apart.

7. The needleless luer access connector of claim 6 wherein the two barbs are aligned with the two ribs when a male luer taper is inserted into the slit.

* * * * *